(12) United States Patent
Zampella et al.

(10) Patent No.: US 11,332,450 B2
(45) Date of Patent: May 17, 2022

(54) ISOXAZOLE AS FXR RECEPTOR AGONISTS

(71) Applicant: Bar Pharmaceuticals Societa' A Responsabilita' Limitata, Reggio Emilia (IT)

(72) Inventors: Angela Zampella, Naples (IT); Stefano Fiorucci, Perugia (IT)

(73) Assignee: Bar Pharmaceuticals Societa' A Responsabilita' Limitata, Reggio Emilia (IT)

( * ) Notice: Subject to any disclaimer, the term of this patent is extended or adjusted under 35 U.S.C. 154(b) by 0 days.

(21) Appl. No.: 17/260,596

(22) PCT Filed: Jul. 17, 2019

(86) PCT No.: PCT/IB2019/056114
§ 371 (c)(1),
(2) Date: Jan. 15, 2021

(87) PCT Pub. No.: WO2020/016801
PCT Pub. Date: Jan. 23, 2020

(65) Prior Publication Data
US 2021/0269409 A1    Sep. 2, 2021

(30) Foreign Application Priority Data

Jul. 17, 2018  (IT) .................. 102018000007265

(51) Int. Cl.
*C07D 261/08*    (2006.01)
(52) U.S. Cl.
CPC .................. *C07D 261/08* (2013.01)
(58) Field of Classification Search
None
See application file for complete search history.

(56) References Cited

U.S. PATENT DOCUMENTS

| 10,080,743 | B2 * | 9/2018 | Or ................. | C07D 261/08 |
| 10,144,729 | B2 * | 12/2018 | Or ................. | C07D 413/12 |
| 10,149,835 | B2 * | 12/2018 | Or ................. | C07D 213/127 |
| 2003/0187042 | A1 * | 10/2003 | Bauer ............ | C07D 261/08 514/378 |
| 2006/0258725 | A1 * | 11/2006 | Boggs ........... | A61P 43/00 514/378 |
| 2013/0261108 | A1 * | 10/2013 | Tully ............. | A61K 31/454 514/217.1 |

FOREIGN PATENT DOCUMENTS

| WO | WO 2004/048349 A1 | 6/2004 |
| WO | WO 2012/087520 A1 | 6/2012 |
| WO | WO 2017/189663 A1 | 11/2017 |

OTHER PUBLICATIONS

Sepe, Valentina et al.: "Novel Isoxazole Derivatives with Potent FXR Agonistic Activity Prevent Acetaminophen-Induced Liver Injury," *ACS Medicinal Chemistry Letters*, vol. 10, No. 4, Dec. 6, 2018, pp. 407-412.
Ma, Yongjie et al.: "Synthetic FXR Agonist GW4064 Prevents Diet-Induced Hepatic Steatosis and Insulin Resistance," *Pharmaceutical Research*, vol. 30, No. 5, Feb. 1, 2013, pp. 1447-1457.
Misawa, Takashi et al.: "Discovery and structural development of small molecules that enhance transport activity of bile salt export pump mutant associated with progressive familial intahepatic cholestasis type 2," *Bioorganic & Medicinal Chemistry*, vol. 20, No. 9, Mar. 14, 2012, pp. 2940-2949.
International Search Report and Written Opinion prepared for International Application PCT/IB2019/056114 by the European Patent Office, acting as the International Searching Authority, dated Oct. 22, 2019.
Fiorucci, Stefano et al.: "Targeting FXR in cholestasis: hype or hope," *Expert Opinion on Therapeutic Targets*, vol. 18, Issue 12, 2014, pp. 1449-1459.

* cited by examiner

*Primary Examiner* — Amy C Bonaparte
(74) *Attorney, Agent, or Firm* — McCarter & English, LLP

(57) ABSTRACT

The present invention related to compounds of formula (I), to pharmaceutical compositions thereof and to their uses, in particular in the treatment and/or prevention of FXR mediated diseases.

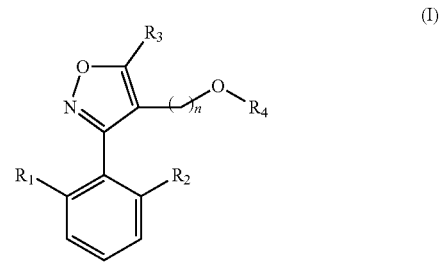

(I)

7 Claims, No Drawings
Specification includes a Sequence Listing.

SEQUENCE LISTING

<160> NUMBER OF SEQ ID NOS: 12

<210> SEQ ID NO 1
<211> LENGTH: 18
<212> TYPE: DNA
<213> ORGANISM: Artificial Sequence
<220> FEATURE:
<223> OTHER INFORMATION: forward primer

<400> SEQUENCE: 1
gaaggtgaag gtcggagt                                              18

<210> SEQ ID NO 2
<211> LENGTH: 22

```
<212> TYPE: DNA
<213> ORGANISM: Artificial Sequence
<220> FEATURE:
<223> OTHER INFORMATION: reverse primer

<400> SEQUENCE: 2
catgggtgga atcatattgg aa                                          22

<210> SEQ ID NO 3
<211> LENGTH: 20
<212> TYPE: DNA
<213> ORGANISM: Artificial Sequence
<220> FEATURE:
<223> OTHER INFORMATION: Forward primer

<400> SEQUENCE: 3
gctgtctgga gtccttctgg                                             20

<210> SEQ ID NO 4
<211> LENGTH: 21
<212> TYPE: DNA
<213> ORGANISM: Artificial Sequence
<220> FEATURE:
<223> OTHER INFORMATION: reverse primer

<400> SEQUENCE: 4
ccaatgatag ggcgaaagaa g                                           21

<210> SEQ ID NO 5
<211> LENGTH: 22
<212> TYPE: DNA
<213> ORGANISM: Artificial Sequence
<220> FEATURE:
<223> OTHER INFORMATION: Forward primer

<400> SEQUENCE: 5
ctgagtatgt cgtggagtct ac                                          22

<210> SEQ ID NO 6
<211> LENGTH: 22
<212> TYPE: DNA
<213> ORGANISM: Artificial Sequence
<220> FEATURE:
<223> OTHER INFORMATION: reverse primer

<400> SEQUENCE: 6
gttggtggtg caggatgcat tg                                          22

<210> SEQ ID NO 7
<211> LENGTH: 20
<212> TYPE: DNA
<213> ORGANISM: Artificial Sequence
<220> FEATURE:
<223> OTHER INFORMATION: Forward primer

<400> SEQUENCE: 7
acgatcctct tcaacccaga                                             20

<210> SEQ ID NO 8
<211> LENGTH: 20
<212> TYPE: DNA
```

```
<210> SEQ ID NO 9
<211> LENGTH: 20
<212> TYPE: DNA
<213> ORGANISM: Artificial Sequence
<220> FEATURE:
<223> OTHER INFORMATION: reverse primer

<400> SEQUENCE: 8
agggctccaa gacttcacac                                               20

<210> SEQ ID NO 9
<211> LENGTH: 20
<212> TYPE: DNA
<213> ORGANISM: Artificial Sequence
<220> FEATURE:
<223> OTHER INFORMATION: forward primer

<400> SEQUENCE: 9
agcttccagg gtttcagaca                                               20

<210> SEQ ID NO 10
<211> LENGTH: 20
<212> TYPE: DNA
<213> ORGANISM: Artificial Sequence
<220> FEATURE:
<223> OTHER INFORMATION: reverse primer

<400> SEQUENCE: 10
cttccaacag gtctgcatga                                               20

<210> SEQ ID NO 11
<211> LENGTH: 20
<212> TYPE: DNA
<213> ORGANISM: Artificial Sequence
<220> FEATURE:
<223> OTHER INFORMATION: forward primer

<400> SEQUENCE: 11
gatgcttccc aagttcaagg                                               20

<210> SEQ ID NO 12
<211> LENGTH: 20
<212> TYPE: DNA
<213> ORGANISM: Artificial Sequence
<220> FEATURE:
<223> OTHER INFORMATION: reverse primer

<400> SEQUENCE: 12
taaagaggaa ggcgatgagc                                               20
```

ISOXAZOLE AS FXR RECEPTOR AGONISTS

CROSS-REFERENCE TO RELATED APPLICATIONS

This patent application is the National Stage entry under 35 U.S.C. § 371 of International Application Number PCT/IB2019/056114 filed on Jul. 17, 2019, published on Jan. 23, 2020 under publication number WO 2020/016801 A1, which claims the benefit of priority under 35 U.S.C. § 119 of Italian patent application no. 102018000007265 filed on Jul. 17, 2018, the entire disclosure of which is incorporated herein by reference.

TECHNICAL FIELD

The present invention relates to isoxazole derivatives and their uses, in particular in the treatment and/or prevention of FXR mediated diseases.

BACKGROUND OF THE INVENTION

Farnesoid X receptor (FXR, also known as BAR, NR1H4) is a ligand-dependent transcription factor and belongs to the super-family of nuclear hormone receptors.

Highly expressed in entero-hepatic tissues (liver and intestine), FXR regulates bile acid homeostasis, lipoprotein, glucose metabolism, liver regeneration and cardiovascular disorders (Mangelsdorf, D. J. et al. Cell 1995, 83; 835; Forman, B. M. et al. Cell 1995, 81, 687; Makishima, M. et al. Science 1999, 284, 1362; Parks, D. J. et al. Science 1999, 284, 1365; Wang, H. et al. Mol. Cell 1999, 3, 543; Kuipers, F. et al. Rev. Endocr. Metab. Disord. 2004, 5,319; Zhang et al. Proc. Natl. Acad. Sci. USA 2006, 103, 1006; Matsubara, T. et al. Mol. Cell. Endocrinol. 2013, 368, 17; Claudel, T. et al. Arterioscler. Thromb. Vasc. Biol. 2005, 25, 2020). Specific bile acids bind and activate FXR, the most potent being chenodeoxycholic acid (CDCA), which is an endogenous ligand of FXR and the primary bile acid found in human bile.

In recent years, various potent and selective FXR agonists have been reported, belonging to steroidal and non-steroidal chemical classes, such as 6-ECDCA, GW4064 and Fexaramine. However, several side effects result from advanced clinical trials with dis-regulation in serum lipids observed in patients with diabetes and liver steatosis (Fiorucci S. et al. Expert Opin. Ther. Targets 2014, 18, 1449-59).

In the context of non-steroidal ligand, GW4064 represents a milestone in the field of isoxazole-type FXR agonists.

Indeed, GW4064 showed limited intestinal absorption (<10%) in rats after oral administration, exhibiting a short terminal half-life. Furthermore, the widely delocalized n-electron system in the stilbene moiety is responsible for its UV light instability therefore GW4064 has a potential cell toxicity.

DISCLOSURE OF INVENTION

The object of the present invention is the identification of novel compounds that act as FXR agonists with improved pharmacokinetic properties compared to GW4064.

Said object is achieved by the present invention, relative to selective FXR agonists containing the isoxazole chemical scaffold of claim 1, to a pharmaceutical composition of claim 5, to the uses of claims 6 and 7. Preferred embodiments are set out within the dependent claims.

BEST MODE FOR CARRYING OUT THE INVENTION

The following paragraphs provide definitions of the various chemical moieties of the compounds according to the invention and are intended to apply uniformly through-out the specification and claims unless an otherwise expressly set out definition provides a broader definition.

The term "alkyl", as used herein, refers to saturated aliphatic hydrocarbon groups. Such term includes straight (unbranched) chains or branched chains.

Non-limiting examples of alkyl groups according to the invention are, for example, methyl, ethyl, propyl, isopropyl, n-butyl, iso-butyl, tert-butyl, n-pentyl, iso-pentyl, n-hexyl and the like.

The term "alkoxy" as used herein, refers to an alkyl group that is linked to the remainder of the compound by an oxygen atom.

The term "halogen", as used herein, refers to fluorine, chlorine, bromine and iodine.

Unless otherwise indicated, the term "substituted", as used herein, means that one or more hydrogen atoms of the above mentioned groups are replaced with another non-hydrogen atom or functional group, provided that normal valencies are maintained and that the substitution results in a stable compound.

The term "pharmaceutically acceptable salts" refers to salts of the below identified compounds of Formula (I) that retain the desired biological activity and are accepted by regulatory authorities.

As used herein, the term "salt" refers to any salt of a compound according to the present invention prepared from an inorganic or organic base. Typically, such salts have a physiologically acceptable cation.

Furthermore, the compounds of Formula (I) may form a salt with a base and these salts are included in the present invention, as long as they are pharmaceutically acceptable salts.

The compounds of formula (I) containing acidic protons may be converted into their therapeutically active, non-toxic base addition salt forms, e.g. metal or amine salts, by treatment with appropriate organic and inorganic bases.

Physiologically or pharmaceutically acceptable salts are particularly suitable for medical applications because of their greater aqueous solubility relative to the parent compound.

Pharmaceutically acceptable salts may also be prepared from other salts including other pharmaceutically acceptable salts of the compounds of Formula (I) using conventional methods.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compounds of the invention are within the scope of the invention. The compounds of Formula (I) may readily be isolated in association with solvent molecules by crystallization or evaporation of an appropriate solvent to give the corresponding solvates.

The compounds of Formula (I) may be in crystalline form. In certain embodiments, the crystalline forms of the compounds of Formula (I) are polymorphs.

The subject invention also includes isotopically-labelled compounds, which are identical to those recited in Formula (I) and following, but differ on the fact that one or more atoms are replaced by an atom having an atomic mass or mass number different from the atomic mass or mass number usually found in nature. Examples of isotopes that can be incorporated into the compounds of the invention and pharmaceutically acceptable salts thereof include isotopes of hydrogen, carbon, nitrogen, oxygen, such as $^2$H, $^3$H, $^{11}$C, $^{13}$C, $^{14}$C, $^{15}$N, $^{17}$O, $^{18}$O.

Compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as $^3$H, $^{14}$C are incorporated, are useful in drug and/or substrate tissue distribution assays. Tritiated, i.e. $^3$H, and carbon-14, i.e. $^{14}$C, isotopes are particularly preferred for their ease of preparation and detectability. $^{11}$C isotope is particularly useful in PET (Positron Emission Tomography). Furthermore, substitution with heavier isotopes such as deuterium, i.e. $^2$H, can afford certain therapeutic advantages resulting from greater metabolic stability, for example increased in vivo half-life or reduced dosage requirements and, hence, may be preferred in some circumstances. Isotopically-labelled compounds of Formula (I) of this invention can generally be prepared by carrying out the procedures disclosed in the Schemes and/or in the Examples below, by replacing a non-isotopically-labelled reagent with a readily available isotopically-labelled reagent.

Certain groups/substituents included in the present invention may be present as isomers. Accordingly, in certain embodiments, the compounds of Formula (I) may have axial asymmetries and, correspondingly, they may exist in the form of optical isomers such as an (R)-form, an (S)-form, and the like. The present invention includes within the scope all such isomers, including racemates, enantiomers and mixtures thereof.

In particular, within the scope of the present invention are included all stereoisomeric forms, including enantiomers, diastereoisomers, and mixtures thereof, including racemates, and the general reference to the compounds of Formula (I) includes all the stereoisomeric forms, unless otherwise indicated.

In general, the compounds or salts of the invention should be interpreted as excluding those compounds (if any) which are so chemically unstable, either per se or in water, that they are clearly unsuitable for pharmaceutical use through all administration routes, whether oral, parenteral, or otherwise. Such compounds are known to the skilled chemist.

According to a first aspect of the invention, compounds of Formula (I):

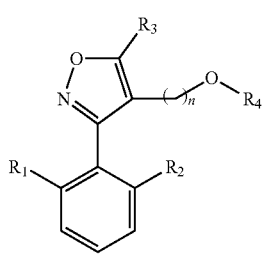

(I)

or pharmaceutically acceptable salts and solvates thereof are provided.

In the compounds of Formula (I):
$R_1$ and $R_2$ are independently selected from the group consisting of H, halogen, and $CF_3$ provided that $R_1$ and $R_2$ are not H at the same time;
$R_3$ is selected from the group consisting of $C_1$-$C_3$alkyl and halo-$C_1$-$C_3$alkyl;
n is an integer selected from 1, 2 and 3;
$R_4$ is selected from the group consisting of phenyl unsubstituted or substituted with one $R_5$ and biphenyl unsubstituted or substituted with one $R_5$;
$R_5$ is selected from the group consisting of $COOR_6$, CN, hydroxy-$C_1$-$C_3$alkyl, $SO_2CH_3$, $CF_3$, $C_1$-$C_3$alkyl-O-phenyl unsubstituted or substituted with one $R_7$ and $C_1$-$C_3$alkyl-O-biphenyl unsubstituted or substituted with one $R_7$;
$R_6$ is selected from the group consisting of H and $C_1$-$C_3$alkyl and
$R_7$ is selected from the group consisting of $COOR_6$, CN, hydroxy-$C_1$-$C_3$alkyl, $SO_2CH_3$ and $CF_3$;
provided that the compound is not 4-((3-(2,6-dichlorophenyl)-5-isopropylisoxazol-4-yl)methoxy)benzoic acid.

According to an embodiment, $R_4$ is selected from the group consisting of

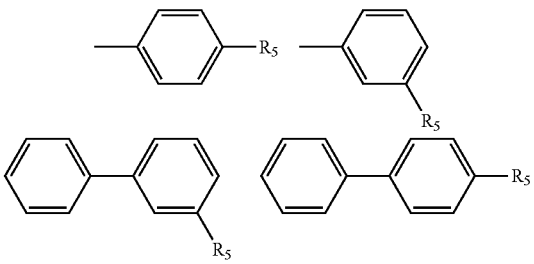

wherein $R_5$ is as defined above.

According to an embodiment, $R_5$ is selected from the group consisting of COOH, $COOCH_3$, CN, —$CH_2OH$, $SO_2CH_3$,

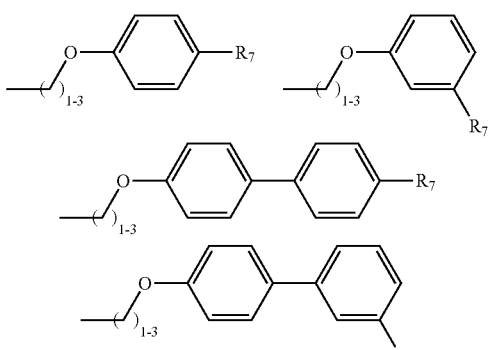

wherein $R_7$ is as defined above.
According to an embodiment, n is 1.
According to an embodiment, $R_1$ and $R_2$ are independently selected from the group consisting of H, Cl and $CF_3$, and preferably, $R_1$ and $R_2$ are chlorine.
According to an embodiment, $R_3$ is selected from the group consisting of methyl, ethyl, propyl, isopropyl, and $CF_3$.
According to an embodiment, $R_7$ is selected from the group consisting of COOH, $COOCH_3$, CN, $CH_2OH$, $SO_2CH_3$ and $CF_3$.

According to an embodiment, the compound of Formula (I) is selected from the group consisting of:

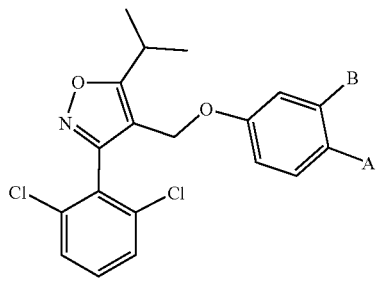

| | | |
|---|---|---|
| A = H | B = H | BAR2101 |
| A = COOMe | B = H | BAR2102 |
| A = CN | B = H | BAR2103 |
| A = CH$_2$OH | B = H | BAR2104 |
| A = CF$_3$ | B = H | BAR2115 |
| A = SO$_2$Me | B = H | BAR2116 |
| A = H | B = COOMe | BAR2110 |
| A = H | B = COOH | BAR2111 |
| A = H | B = CH$_2$OH | BAR2112 |
| A = H | B = CN | BAR2113 |
| A = H | B = CF$_3$ | BAR2114 |
| A = H | B = SO$_2$Me | BAR2117 |

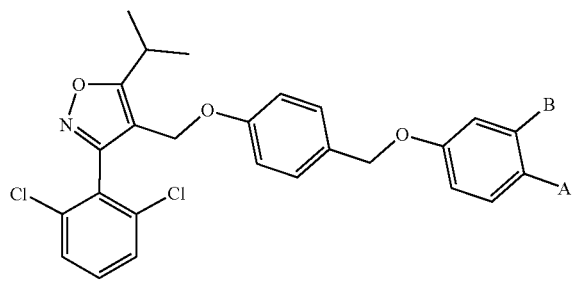

| | | |
|---|---|---|
| A = COOMe | B = H | BAR2106 |
| A = CN | B = H | BAR2107 |
| A = CH$_2$OH | B = H | BAR2108 |
| A = COOH | B = H | BAR2109 |
| A = SO$_2$Me | B = H | BAR2125 |
| A = CF$_3$ | B = H | BAR2126 |
| A = H | B = CN | BAR2121 |
| A = H | B = COOMe | BAR2122 |
| A = H | B = COOH | BAR2123 |
| A = H | B = CH$_2$OH | BAR2124 |
| A = H | B = SO$_2$Me | BAR2127 |
| A = H | B = CF$_3$ | BAR2128 |

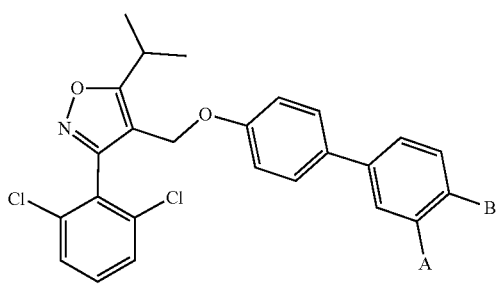

| | | |
|---|---|---|
| A = COOMe | B = H | BAR2118 |
| A = COOH | B = H | BAR2119 |
| A = CH$_2$OH | B = H | BAR2120 |
| A = CN | B = H | BAR2129 |
| A = SO$_2$Me | B = H | BAR2130 |
| A = CF3 | B = H | BAR2131 |
| A = H | B = COOMe | BAR2132 |
| A = H | B = CN | BAR2133 |
| A = H | B = CH$_2$OH | BAR2134 |
| A = H | B = COOH | BAR2135 |

-continued

| | | |
|---|---|---|
| A = H | B = SO₂Me | BAR2136 |
| A = H | B = CF₃ | BAR2137 |

| | | |
|---|---|---|
| A = COOMe | B = H | BAR2138 |
| A = COOH | B = H | BAR2139 |
| A = CH₂OH | B = H | BAR2140 |
| A = CN | B = H | BAR2141 |
| A = SO₂Me | B = H | BAR2142 |
| A = CF₃ | B = H | BAR2143 |
| A = H | B = COOMe | BAR2144 |
| A = H | B = CN | BAR2145 |
| A = H | B = CH₂OH | BAR2146 |
| A = H | B = COOH | BAR2147 |
| A = H | B = SO₂Me | BAR2148 |
| A = H | B = CF₃ | BAR2149 |

| | | |
|---|---|---|
| A = COOMe | B = H | BAR2150 |
| A = COOH | B = H | BAR2151 |
| A = CH₂OH | B = H | BAR2152 |
| A = CN | B = H | BAR2153 |
| A = SO₂Me | B = H | BAR2154 |
| A = CF₃ | B = H | BAR2155 |
| A = H | B = COOMe | BAR2156 |
| A = H | B = CN | BAR2157 |
| A = H | B = CH₂OH | BAR2158 |
| A = H | B = COOH | BAR2159 |
| A = H | B = SO₂Me | BAR2160 |
| A = H | B = CF₃ | BAR2161 |

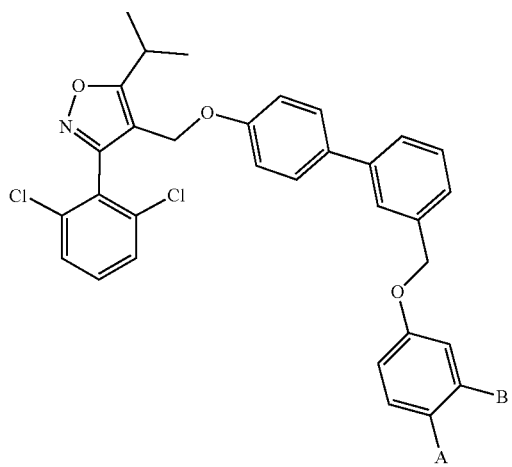
| | | |
|---|---|---|
| A = COOMe | B = H | BAR2162 |
| A = COOH | B = H | BAR2163 |
| A = CH₂OH | B = H | BAR2164 |
| A = CN | B = H | BAR2165 |
| A = SO₂Me | B = H | BAR2166 |
| A = CF₃ | B = H | BAR2167 |
| A = H | B = COOMe | BAR2168 |
| A = H | B = CN | BAR2169 |
| A = H | B = CH₂OH | BAR2170 |
| A = H | B = COOH | BAR2171 |
| A = H | B = SO₂Me | BAR2172 |
| A = H | B = CF₃ | BAR2173 |
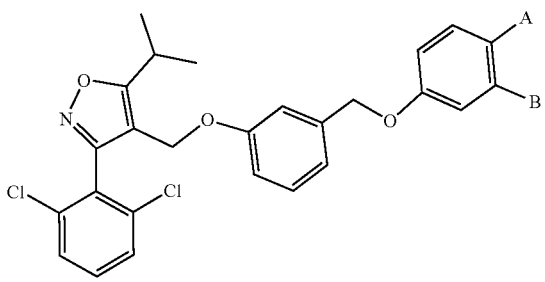
| | | |
|---|---|---|
| A = COOMe | B = H | BAR2174 |
| A = COOH | B = H | BAR2175 |
| A = CH₂OH | B = H | BAR2176 |
| A = CN | B = H | BAR2177 |
| A = SO₂Me | B = H | BAR2178 |
| A = CF₃ | B = H | BAR2179 |
| A = H | B = COOMe | BAR2180 |
| A = H | B = CN | BAR2181 |
| A = H | B = CH₂OH | BAR2182 |
| A = H | B = COOH | BAR2183 |
| A = H | B = SO₂Me | BAR2184 |
| A = H | B = CF₃ | BAR2185 |

-continued
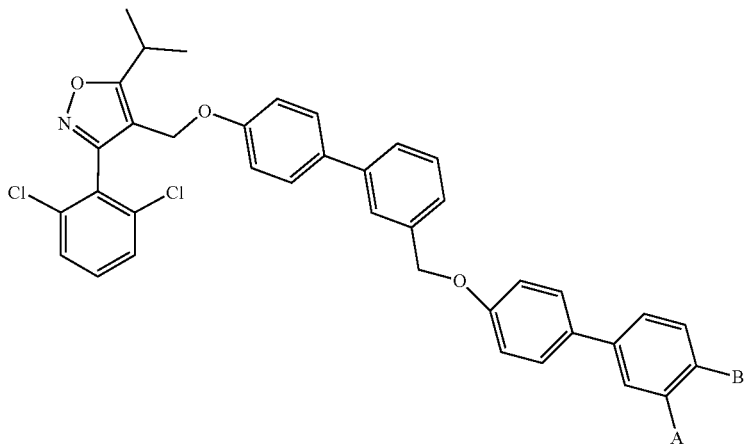
| | | |
|---|---|---|
| A = COOMe | B = H | BAR2186 |
| A = COOH | B = H | BAR2187 |
| A = CH₂OH | B = H | BAR2188 |
| A = CN | B = H | BAR2189 |
| A = SO₂Me | B = H | BAR2190 |
| A = CF₃ | B = H | BAR2191 |
| A = H | B = COOMe | BAR2192 |
| A = H | B = CN | BAR2193 |
| A = H | B = CH₂OH | BAR2194 |
| A = H | B = COOH | BAR2195 |
| A = H | B = SO₂Me | BAR2196 |
| A = H | B = CF₃ | BAR2197 |
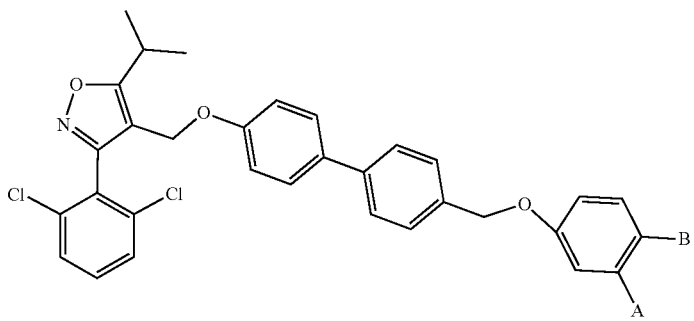
| | | |
|---|---|---|
| A = COOMe | B = H | BAR2198 |
| A = COOH | B = H | BAR2199 |
| A = CH₂OH | B = H | BAR2200 |
| A = CN | B = H | BAR2201 |
| A = SO₂Me | B = H | BAR2202 |
| A = CF₃ | B = H | BAR2203 |
| A = H | B = COOMe | BAR2204 |
| A = H | B = CN | BAR2205 |
| A = H | B = CH₂OH | BAR2206 |
| A = H | B = COOH | BAR2207 |
| A = H | B = SO₂Me | BAR2208 |
| A = H | B = CF₃ | BAR2209 |

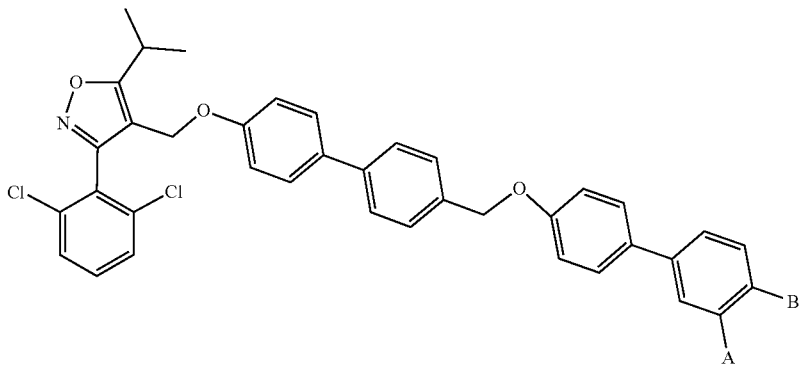

| | | |
|---|---|---|
| A = COOMe | B = H | BAR2210 |
| A = COOH | B = H | BAR2211 |
| A = CH$_2$OH | B = H | BAR2212 |
| A = CN | B = H | BAR2213 |
| A = SO$_2$Me | B = H | BAR2214 |
| A = CF$_3$ | B = H | BAR2215 |
| A = H | B = COOMe | BAR2216 |
| A = H | B = CN | BAR2217 |
| A = H | B = CH$_2$OH | BAR2218 |
| A = H | B = COOH | BAR2219 |
| A = H | B = SO$_2$Me | BAR2220 |
| A = H | B = CF$_3$ | BAR2221 |

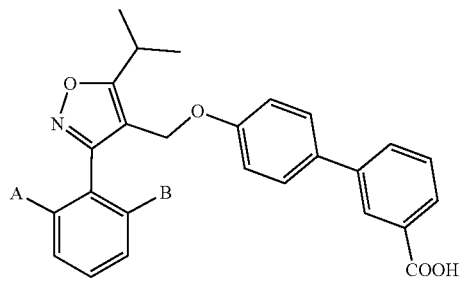

| | | |
|---|---|---|
| A = H | B = Cl | BAR2222 |
| A = H | B = Br | BAR2223 |
| A = H | B = CF$_3$ | BAR2224 |
| A = Br | B = Cl | BAR2225 |
| A = Br | B = Br | BAR2226 |

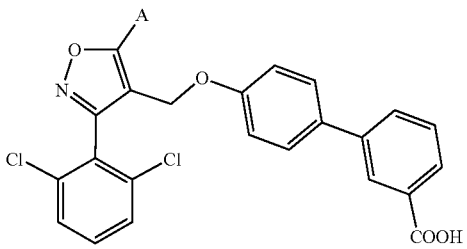

| | |
|---|---|
| A = –CH$_3$ | BAR2227 |
| A = –(CH$_2$)$_2$CH$_3$ | BAR2228 |

A second aspect of the present invention relates to a pharmaceutical composition comprising a compound of Formula (I) as disclosed above, included 4-((3-(2,6-dichlorophenyl)-5-isopropylisoxazol-4-yl)methoxy)benzoic acid, and at least one pharmaceutically acceptable excipient.

A person skilled in the art is aware of a whole variety of such excipient compounds suitable to formulate a pharmaceutical composition.

The compounds of the invention, together with a conventionally employed excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral administration (including subcutaneous and intravenous use).

Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

Pharmaceutical compositions containing a compound of this invention can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of the present invention can be administered by a variety of routes including oral, rectal, subcutaneous, intravenous, intramuscular, intranasal and pulmonary routes. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include pre-filled, pre-measured ampoules or syringes of the liquid compositions or pills, tablets, capsules or the like in the case of solid compositions.

Liquid forms suitable for oral administration may include a suitable aqueous or non-aqueous vehicle with buffers, suspending and dispensing agents, colorants, flavours and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel or corn starch; a lubricant such as magnesium stearate; a glidant such as colloidal silicon dioxide; a sweetening agent such as sucrose or saccharin; or a flavouring agent such as peppermint, methyl salicylate, or orange flavouring.

Injectable compositions are typically based upon injectable sterile saline or phosphate-buffered saline or other injectable carriers known in the art.

The pharmaceutical compositions may be in the form of tablets, pills, capsules, solutions, suspensions, emulsion, powders, suppository and as sustained release formulations.

If desired, tablets may be coated by standard aqueous or non-aqueous techniques. In certain embodiments, such compositions and preparations can contain at least 0.1 percent of active compound. The percentage of active compound in these compositions may, of course, be varied and may conveniently be between about 1 percent to about 60 percent of the weight of the unit. The amount of active compound in such therapeutically useful compositions is such that therapeutically active dosage will be obtained. The active compounds can also be administered intranasal as, for example, liquid drops or spray.

The tablets, pills, capsules, and the like may also contain a binder such as gum tragacanth, acacia, corn starch or gelatin; excipients such as calcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil. Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propyl parabens as preservatives, a dye and a flavoring agent such as cherry or orange flavor. To prevent breakdown during transit through the upper portion of the gastrointestinal tract, the composition be an enteric coated formulation.

Compositions for pulmonary administration include, but are not limited to, dry powder compositions consisting of the powder of a compound of Formula (I) or a salt thereof, and the powder of a suitable carrier and/or lubricant. The compositions for pulmonary administration can be inhaled from any suitable dry powder inhaler device known to a person skilled in the art.

Administration of the compositions is performed under a protocol and at a dosage sufficient to reduce the inflammation and pain in the subject. In some embodiments, in the pharmaceutical compositions of the present invention the active principle or active principles are generally formulated in dosage units. The dosage unit may contain from 0.1 to 1000 mg of a compound of Formula (I) per dosage unit for daily administration.

In some embodiments, the amounts effective for a specific formulation will depend on the severity of the disease, disorder or condition, previous therapy, the individual's health status and response to the drug. In some embodiments, the dose is in the range from 0.001% by weight to about 60% by weight of the formulation.

When used in combination with one or more other active ingredients, the compound of the present invention and the other active ingredient may be used in lower doses than when each is used singly.

Concerning formulations with respect to any variety of routes of administration, methods and formulations for the administration of drugs are disclosed in Remington's Pharmaceutical Sciences, 17th Edition, Gennaro et al. Eds., Mack Publishing Co., 1985, and Remington's Pharmaceutical Sciences, Gennaro A R ed. 20th Edition, 2000, Williams & Wilkins PA, USA, and Remington: The Science and Practice of Pharmacy, 21st Edition, Lippincott Williams & Wilkins Eds., 2005; and in Loyd V. Allen and Howard C. Ansel, Ansel's Pharmaceutical Dosage Forms and Drug Delivery Systems, 10th Edition, Lippincott Williams & Wilkins Eds., 2014.

The above described components for orally administered or injectable compositions are merely representative.

The compounds of this invention can also be administered in sustained release forms or from sustained release drug delivery systems.

A third aspect of the present invention relates to a compound of Formula (I) as disclosed above, included 4-((3-(2, 6-dichlorophenyl)-5-isopropylisoxazol-4-yl)methoxy) benzoic acid, for the use as a medicament.

A compound of Formula (I) as disclosed above, included 4-((3-(2,6-dichlorophenyl)-5-isopropylisoxazol-4-yl) methoxy) benzoic acid, can be used in the prevention and/or treatment of a disorder selected from the group consisting of gastrointestinal disorders, liver disorders, cardiovascular disorders, vascular disorders, pulmonary disorders, metabolic pathologies, infectious diseases, cancer, renal disorders, inflammatory disorders including immune-mediated, and neurological disorders.

In one embodiment, the immune-mediated inflammatory disorders include autoimmune disorders such as systemic lupus erythematosus, rheumatoid arthritis, Sjögren's syndrome, scleroderma also known as systemic sclerosis, spondyloarthritis, vasculitis, sarcoidosis, Mediterranean fever, and other hereditary autoinflammatory diseases, polymyositis and dermatomyositis, Behcet's syndrome.

In one embodiment, the infectious diseases are selected from the group of Acquired Immuno-Deficiency Syndrome (AIDS) and related disorders, virus B and virus C infections.

In one embodiment, neurological disorders include Alzheimer's disease and other forms of dementia, Parkinson and other movement disorders, amyotrophic lateral sclerosis and other motor neuron disorders, multiple sclerosis and other demyelinating diseases, ischemic stroke, myasthenia and muscular dystrophy.

In one embodiment, the liver disorders include primary biliary cirrhosis (PBC), cerebrotendinous xanthomatosis (CTX), primary sclerosing cholangitis (PSC), drug induced cholestasis, intrahepatic cholestasis of pregnancy, parenteral nutrition associated cholestasis, bacterial overgrowth or sepsis associated cholestasis, autoimmune hepatitis, chronic viral hepatitis, alcoholic liver disease, nonalcoholic fatty liver disease (NAFLD), nonalcoholic steatohepatitis (NASH), liver transplant, congenital hepatic fibrosis, granulomatous liver disease, intra- or extrahepatic malignancy, Wilson's disease, hemochromatosis, and alpha 1-antitrypsin deficiency.

In one embodiment, the gastrointestinal disorders include inflammatory bowel disease (IBD) (including Crohn's disease, ulcerative colitis and undetermined colitis), irritable bowel syndrome (IBS), bacterial overgrowth, acute and chronic pancreatitis, malabsorption, post-radiation colitis, and microscopic colitis.

In one embodiment, the renal disorders include diabetic nephropathy, hypertensive nephropathy, chronic glomerulonephritis including chronic transplant glomerulonephritis, chronic tubule interstitial diseases and vascular disorders of the kidney.

In one embodiment, the cardiovascular diseases include atherosclerosis, arteriosclerosis, dyslipidemia, hypercholesterolemia, hypertriglyceridemia, hypertension also known as arterial hypertension, inflammatory heart diseases including myocarditis and endocarditis, ischemic heart disease, stable angina, unstable angina, myocardial infarction, cerebrovascular diseases including ischemic stroke.

In one embodiment, the vascular diseases include pulmonary heart disease such as pulmonary hypertension, peripheral artery disease (PAD), also known as peripheral vascular disease (PVD) peripheral artery occlusive disease, and peripheral obliterative arteriopathy.

In one embodiment, pulmonary disorders include asthma, cystic fibrosis, obstructive respiratory diseases, interstitial lung disease including, but not limited to, primary or secondary pulmonary fibrosis.

In one embodiment, the metabolic disease is selected from the group of diseases comprising insulin resistance, metabolic syndrome, Type I and Type II diabetes, hypoglycaemia, disorders of the adrenal cortex including adrenal cortex insufficiency. Metabolic diseases also include obesity and conditions associated with bariatric surgery.

In one embodiment, cancer is selected from the group comprising liver cancer, bile duct cancers, oesophageal cancer, pancreatic cancer, gastric cancer, colon-rectal cancer, breast cancer, ovarian cancer and the condition associated with chemotherapy resistance.

Compounds of Formula (I) that can be used as a medicament and for the prevention and/or treatment of the disorders listed above are selected from the group consisting of

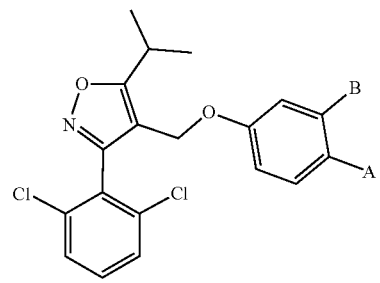

| | | |
|---|---|---|
| A = H | B = H | BAR2101 |
| A = COOMe | B = H | BAR2102 |
| A = CN | B = H | BAR2103 |
| A = CH$_2$OH | B = H | BAR2104 |
| A = COON | B = H | BAR2105 |
| A = CF$_3$ | B = H | BAR2115 |
| A = SO$_2$Me | B = H | BAR2116 |
| A = H | B = COOMe | BAR2110 |
| A = H | B = COOH | BAR2111 |
| A = H | B = CH$_2$OH | BAR2112 |
| A = H | B = CN | BAR2113 |
| A = H | B = CF$_3$ | BAR2114 |
| A = H | B = SO$_2$Me | BAR2117 |

-continued

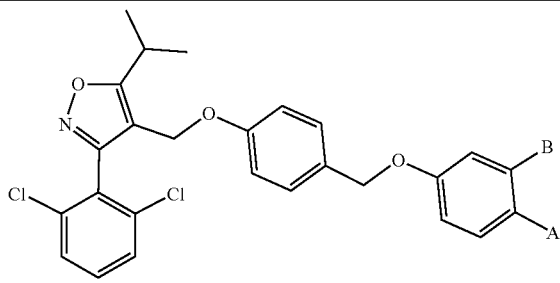

| | | |
|---|---|---|
| A = COOMe | B = H | BAR2106 |
| A = CN | B = H | BAR2107 |
| A = CH$_2$OH | B = H | BAR2108 |
| A = COOH | B = H | BAR2109 |
| A = SO$_2$Me | B = H | BAR2125 |
| A = CF$_3$ | B = H | BAR2126 |
| A = H | B = CN | BAR2121 |
| A = H | B = COOMe | BAR2122 |
| A = H | B = COOH | BAR2123 |
| A = H | B = CH$_2$OH | BAR2124 |
| A = H | B = SO$_2$Me | BAR2127 |
| A = H | B = CF$_3$ | BAR2128 |

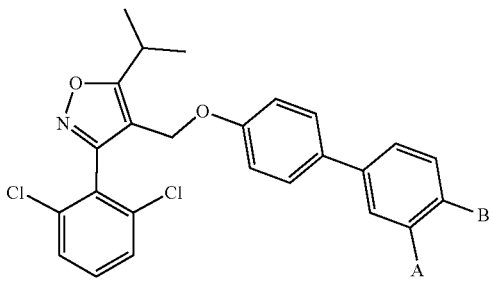

| | | |
|---|---|---|
| A = COOMe | B = H | BAR2118 |
| A = COON | B = H | BAR2119 |
| A = CH$_2$OH | B = H | BAR2120 |
| A = CN | B = H | BAR2129 |
| A = SO$_2$Me | B = H | BAR2130 |
| A = CF$_3$ | B = H | BAR2131 |
| A = H | B = COOMe | BAR2132 |
| A = H | B = CN | BAR2133 |
| A = H | B = CH$_2$OH | BAR2134 |
| A = H | B = COOH | BAR2135 |
| A = H | B = SO$_2$Me | BAR2136 |
| A = H | B = CF$_3$ | BAR2137 |

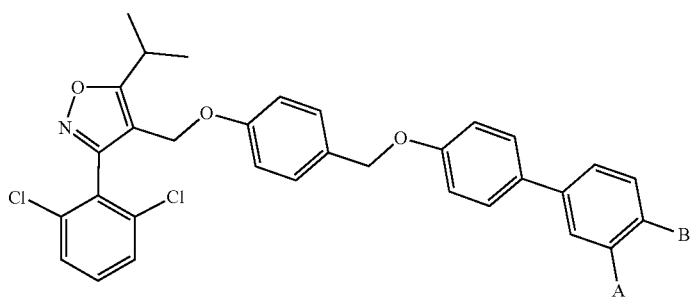

| | | |
|---|---|---|
| A = COOMe | B = H | BAR2138 |
| A = COOH | B = H | BAR2139 |
| A = CH$_2$OH | B = H | BAR2140 |
| A = CN | B = H | BAR2141 |
| A = SO$_2$Me | B = H | BAR2142 |
| A = CF$_3$ | B = H | BAR2143 |
| A = H | B = COOMe | BAR2144 |
| A = H | B = CN | BAR2145 |
| A = H | B = CH$_2$OH | BAR2146 |

| | | |
|---|---|---|
| A = H | B = COOH | BAR2147 |
| A = H | B = SO₂Me | BAR2148 |
| A = H | B = CF₃ | BAR2149 |

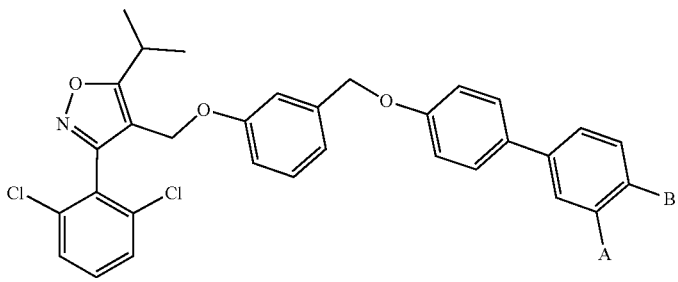

| | | |
|---|---|---|
| A = COOMe | B = H | BAR2150 |
| A = COOH | B = H | BAR2151 |
| A = CH₂OH | B = H | BAR2152 |
| A = CN | B = H | BAR2153 |
| A = SO₂Me | B = H | BAR2154 |
| A = CF₃ | B = H | BAR2155 |
| A = H | B = COOMe | BAR2156 |
| A = H | B = CN | BAR2157 |
| A = H | B = CH₂OH | BAR2158 |
| A = H | B = COOH | BAR2159 |
| A = H | B = SO₂Me | BAR2160 |
| A = H | B = CF₃ | BAR2161 |

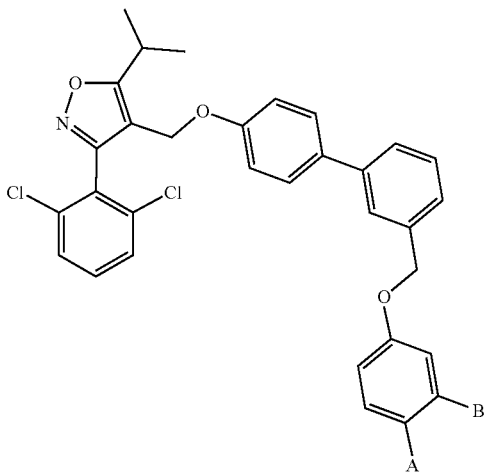

| | | |
|---|---|---|
| A = COOMe | B = H | BAR2162 |
| A = COOH | B = H | BAR2163 |
| A = CH₂OH | B = H | BAR2164 |
| A = CN | B = H | BAR2165 |
| A = SO₂Me | B = H | BAR2166 |
| A = CF₃ | B = H | BAR2167 |
| A = H | B = COOMe | BAR2168 |
| A = H | B = CN | BAR2169 |
| A = H | B = CH₂OH | BAR2170 |
| A = H | B = COOH | BAR2171 |
| A = H | B = SO₂Me | BAR2172 |
| A = H | B = CF₃ | BAR2173 |

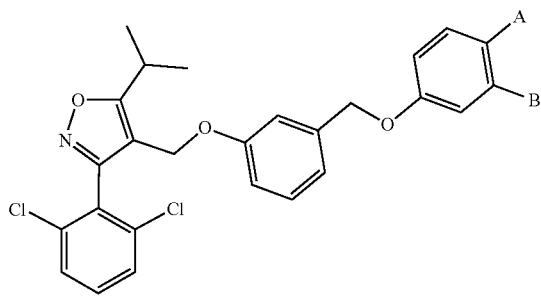
| | | |
|---|---|---|
| A = COOMe | B = H | BAR2174 |
| A = COOH | B = H | BAR2175 |
| A = CH₂OH | B = H | BAR2176 |
| A = CN | B = H | BAR2177 |
| A = SO₂Me | B = H | BAR2178 |
| A = CF₃ | B = H | BAR2179 |
| A = H | B = COOMe | BAR2180 |
| A = H | B = CN | BAR2181 |
| A = H | B = CH₂OH | BAR2182 |
| A = H | B = COOH | BAR2183 |
| A = H | B = SO₂Me | BAR2184 |
| A = H | B = CF₃ | BAR2185 |
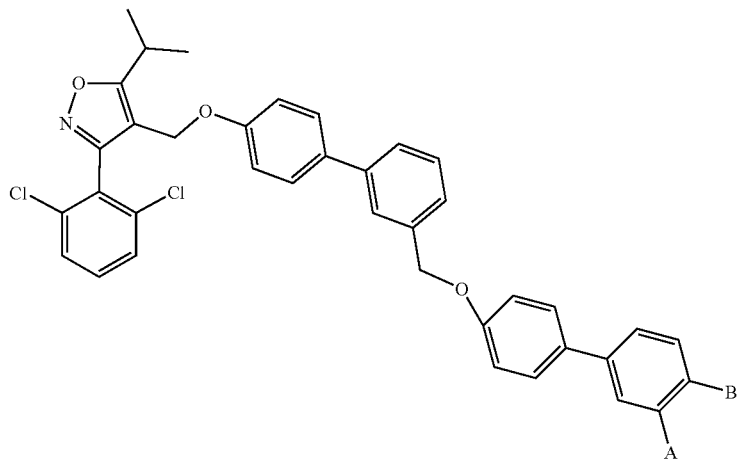
| | | |
|---|---|---|
| A = COOMe | B = H | BAR2186 |
| A = COOH | B = H | BAR2187 |
| A = CH₂OH | B = H | BAR2188 |
| A = CN | B = H | BAR2189 |
| A = SO₂Me | B = H | BAR2190 |
| A = CF₃ | B = H | BAR2191 |
| A = H | B = COOMe | BAR2192 |
| A = H | B = CN | BAR2193 |
| A = H | B = CH₂OH | BAR2194 |
| A = H | B = COOH | BAR2195 |
| A = H | B = SO₂Me | BAR2196 |
| A = H | B = CF₃ | BAR2197 |
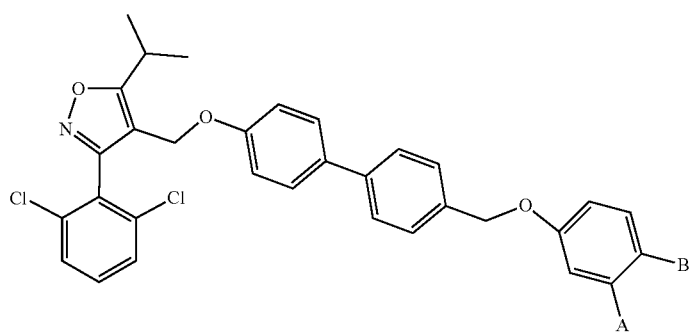

-continued

| | | |
|---|---|---|
| A = COOMe | B = H | BAR2198 |
| A = COOH | B = H | BAR2199 |
| A = CH$_2$OH | B = H | BAR2200 |
| A = CN | B = H | BAR2201 |
| A = SO$_2$Me | B = H | BAR2202 |
| A = CF$_3$ | B = H | BAR2203 |
| A = H | B = COOMe | BAR2204 |
| A = H | B = CN | BAR2205 |
| A = H | B = CH$_2$OH | BAR2206 |
| A = H | B = COOH | BAR2207 |
| A = H | B = SO$_2$Me | BAR2208 |
| A = H | B = CF$_3$ | BAR2209 |

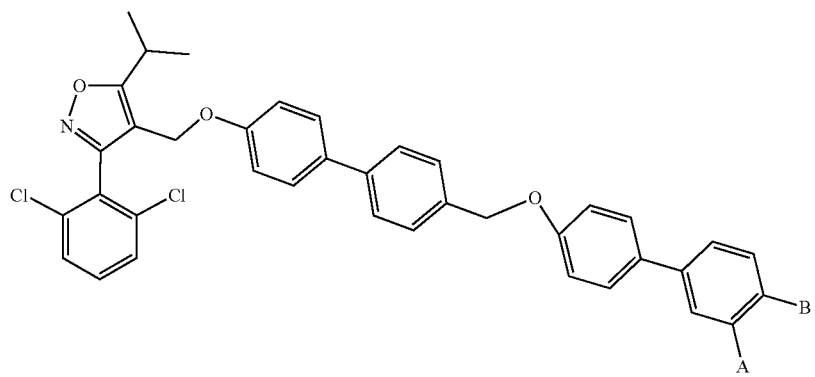

| | | |
|---|---|---|
| A = COOMe | B = H | BAR2210 |
| A = COOH | B = H | BAR2211 |
| A = CH$_2$OH | B = H | BAR2212 |
| A = CN | B = H | BAR2213 |
| A = SO$_2$Me | B = H | BAR2214 |
| A = CF$_3$ | B = H | BAR2215 |
| A = H | B = COOMe | BAR2216 |
| A = H | B = CN | BAR2217 |
| A = H | B = CH$_2$OH | BAR2218 |
| A = H | B = COOH | BAR2219 |
| A = H | B = SO$_2$Me | BAR2220 |
| A = H | B = CF$_3$ | BAR2221 |

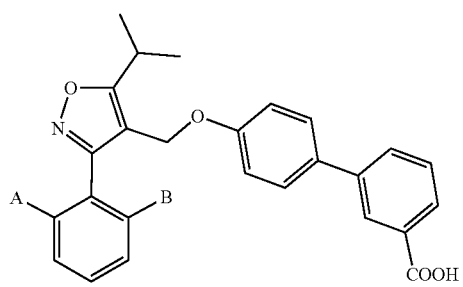

| | | |
|---|---|---|
| A = H | B = Cl | BAR2222 |
| A = H | B = Br | BAR2223 |
| A = H | B = CF$_3$ | BAR2224 |
| A = Br | B = Cl | BAR2225 |
| A = Br | B = Br | BAR2226 |

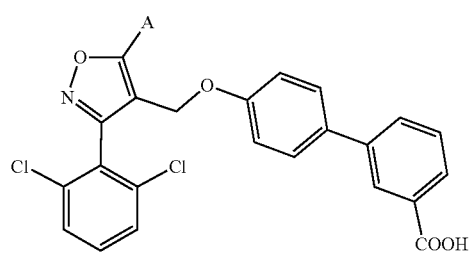

| | |
|---|---|
| A = −CH$_3$ | BAR2227 |
| A = −(CH$_2$)$_2$CH$_3$ | BAR2228 |

Further characteristics of the present invention will result from the following description of some merely illustrative and non-limiting examples.

The following abbreviations are used in the attached examples.

Methylene chloride ($CH_2Cl_2$), hydroxylamine hydrochloride ($NH_2OH$), methanol (MeOH), potassium carbonate ($K_2CO_3$), sodium sulphate ($Na_2SO_4$), N,N-Diisopropylethylamine (DIPEA), dimethylformamide (DMF), (2-(1H-benzotriazol-1-yl)-1,1,3,3-tetramethyluronium hexafluorophosphate (HBTU), lithium bromide (LiBr), sodium bicarbonate ($NaHCO_3$), trifluoroacetic acid (TFA), tetrahydrofuran (THF), lithium hydroxide (LiOH), hydrochloric acid (HCl), ethyl acetate (EtOAc), nitrogen ($N_2$), water ($H_2O$), hour (h), room temperature (rt), retention time ($t_R$).

When not otherwise indicated, $^1H$ NMR was recorded on Varian Inova 400 MHz, using $CDCl_3$ as solvent, and $^{13}C$ NMR was recorded on Varian Inova 100 MHz, using $CDCl_3$ as solvent.

EXAMPLES

Example 1. Preparation of BAR2101-2105, BAR2110-2113, BAR2116, BAR2118-2120

Alcohol 1 was prepared in a multi-step procedure, involving aldehyde oxime formation, chlorination, base promoted β-ketoester mediated isoxazole formation and diisobutyl aluminum hydride mediated ester reduction, as previously described (Cipriani, S. et al. Sci. Rep. 2017, 7, 41055). Then, the key intermediate primary alcohol 1 was utilized in multiple Mitsunobu reactions with various phenols (Scheme 1) to produce BAR2101-BAR2103, BAR2110, BAR2113, BAR2116, and BAR2118 in high chemical yields.

$LiBH_4$ reduction and basic hydrolysis on methyl esters BAR2102 and BAR2110 afforded the corresponding alcohols BAR2104 (95% yield) and BAR2112 (quantitative yield) and the carboxylic acids BAR2105 (quantitative yield) and BAR2111 (89% yield), respectively.

Mitsunobu reaction on the alcohol 1 with methyl 4'-hydroxy-[1,1'-biphenyl]-3-carboxylate, furnished the constrained methyl ester BAR2118 in 68% yield. Reduction and hydrolysis in the same experimental conditions previously described gave the corresponding alcohol BAR2120 and the carboxylic acid BAR2119 (83% and 64% chemical yield, respectively).

Scheme 1

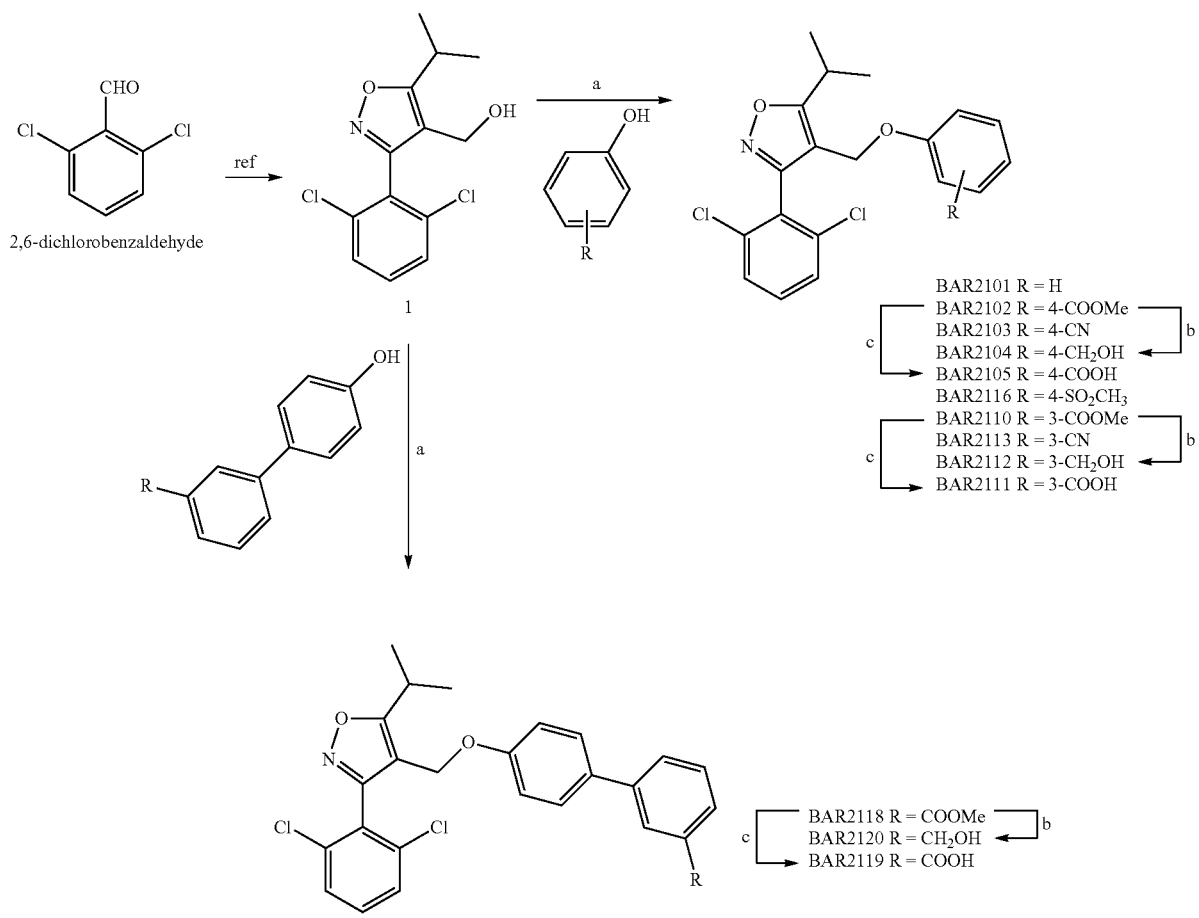

a) PPh$_3$, DIAD, THF dry, 0° C.; b) LiBH$_4$, MeOH dry, THF dry, 0° C.; c) NaOH, MeOH:H$_2$O 1:1 v/v.

General Procedures

Step a). Mitsunobu Reaction.

To a solution of PPh$_3$ (3.5 eq) in dry THF at 0° C., DIAD (3.5 eq) was added dropwise. The suspension was stirred for 10 min, then a solution of compound 1 in dry THF was added. After 10 min, a solution of the corresponding phenol in dry THF was added. After a period of 3 h-overnight, water (10 mL) was added and the reaction mixture was evaporated. The residue was than extracted with EtOAc (3×50 mL). The combined organic layers were washed with a solution of KOH 2.5 M and water, dried and evaporated to give a yellow oil. Purification by flash chromatography on silica gel gave BAR2101-2103, BAR2110, BAR2113, BAR2116, BAR2118.

Step b) LiBH$_4$ Reduction.

To a solution of esters BAR2102, or BAR2110 or BAR2118 in dry THF (25 mL), at 0° C., dry methanol (3.0 eq) and LiBH$_4$ (3.0 eq) were added. The resulting mixture was stirred for 4 h-8 h at 0° C., then it was quenched by addition of 1M NaOH (2.0 eq) and ethyl acetate. The organic phase was washed with water, dried (Na$_2$SO$_4$) and concentrated giving crude residue that was purified with HPLC or silica gel column chromatography.

Step c) Basic Hydrolysis.

Another portion of BAR2102, or BAR2110 or 2118 was hydrolyzed with NaOH (5.0 eq) in a solution of MeOH:H$_2$O 1:1 v/v (30 mL). The mixture was stirred for 8 h under reflux. The resulting solution was then acidified with HCl 6M and extracted with ethyl acetate (3×50 mL). The collected organic phases were washed with brine, dried over Na$_2$SO$_4$ anhydrous and evaporated under reduced pressure to give compound crude residue that was subjected to the purification through HPLC or flash chromatography.

Example 1A. Preparation of 3-(2,6-dichlorophenyl)-5-isopropyl-4-(phenoxymethyl)isoxazole (BAR2101)

Purification by silica gel (hexane and 0.5% TEA) after step a, gave BAR2101 (40%). An analytic sample was obtained by HPLC on a Nucleodur 100-5 C18 (5 μm; 4.6 mm i.d.×250 mm), with MeOH/H$_2$O (82:18) as eluent (flow rate 1 mL/min) ($t_R$=10 min).

BAR2101 C$_{19}$H$_{17}$Cl$_2$NO$_2$ $^1$H NMR (CDCl$_3$, 400 MHz): δ 7.39 (2H, d, J=7.7 Hz), 7.31 (1H, t, J=7.7 Hz), 7.22 (2H, t, J=7.8 Hz), 6.93 (1H, t, J=7.8 Hz), 6.78 (2H, d, J=7.8 Hz), 4.72 (2H, s), 3.33 (1H, septet, J=6.9 Hz), 1.41 (6H, d, J=6.9 Hz); $^{13}$C NMR (CDCl$_3$, 100 MHz) δ 176.3, 159.1, 158.9, 135.8 (2C), 131.2, 129.4 (2C), 128.0 (3C), 121.2, 114.7 (2C), 109.4, 59.2, 27.0, 20.8 (2C).

Example 2A. Preparation of Methyl 4-((3-(2,6-dichlorophenyl)-5-isopropylisoxazol-4-yl)methoxy)benzoate (BAR2102)

Purification by silica gel (9:1 hexane/AcOEt and 0.5% TEA), after step a, gave BAR2102 (82%). An analytic sample was obtained by HPLC on a Nucleodur 100-5 C18 (5 μm; 4.6 mm i.d.×250 mm), with MeOH/H$_2$O (82:18) as eluent (flow rate 1 mL/min) ($t_R$=12 min).

BAR2102 C$_{21}$H$_{19}$Cl$_2$NO$_4$ $^1$H NMR (CDCl$_3$, 400 MHz): δ 7.91 (2H, d, J=8.2 Hz), 7.39 (2H, d, J=7.6 Hz), 7.31 (1H, t, J=7.6 Hz), 6.78 (2H, d, J=8.2 Hz), 4.77 (2H, s), 3.86 (3H, s), 3.32 (1H, septet, J=6.7 Hz), 1.42 (6H, d, J=6.7 Hz); $^{13}$C NMR (CDCl$_3$, 100 MHz): δ 176.5, 166.7, 161.8, 159.0, 135.7 (2C), 131.5, 131.3 (2C), 128.1 (2C), 127.7, 123.0, 114.1 (2C), 108.8, 59.5, 51.9, 27.1, 20.8 (2C).

Example 3A. Preparation of 4-((3-(2,6-dichlorophenyl)-5-isopropylisoxazol-4-yl)methoxy)benzonitrile (BAR2103)

Purification by silica gel (9:1 hexane/AcOEt and 0.5% TEA), after step a, gave BAR2103 (89%). An analytic sample was obtained through purification with by on a Nucleodur 100-5 C18 (5 μm; 4.6 mm i.d.×250 mm), with MeOH/H$_2$O (82:18) as eluent (flow rate 1 mL/min) ($t_R$=7.4 min).

BAR2103 C$_{20}$H$_{16}$Cl$_2$N$_2$O$_2$ $^1$H NMR (CDCl$_3$, 400 MHz): δ 7.52 (2H, d, J=8.5 Hz), 7.40 (2H, d, J=7.0 Hz), 7.33 (1H, t, J=7.0 Hz), 6.81 (2H, d, J=8.5 Hz), 4.77 (2H, s), 3.31 (1H, septet, J=6.8 Hz), 1.42 (6H, d, J=6.8 Hz); $^{13}$C NMR (CDCl$_3$, 100 MHz): δ 176.61, 161.3, 158.9, 135.7 (2C), 133.9 (2C), 131.4, 128.1 (2C), 127.5, 118.9, 115.2 (2C), 108.5, 104.5, 59.5, 27.1, 20.8 (2C).

Example 4A. Preparation of (4-((3-(2,6-dichlorophenyl)-5-isopropylisoxazol-4-yl)methoxy)phenyl)methanol (BAR2104)

Purification by silica gel (100% CH$_2$Cl$_2$), after step b, gave BAR2104 (95%). An analytic sample was obtained by HPLC on a Nucleodur 100-5 C18 (5 μm; 4.6 mm i.d.×250 mm), with MeOH/H$_2$O (70:30) as eluent (flow rate 1 mL/min) ($t_R$=13 min).

BAR2104 C$_{20}$H$_{19}$Cl$_2$NO$_3$ $^1$H NMR (CDCl$_3$, 400 MHz): δ 7.39 (2H, d, J=7.2 Hz), 7.32 (1H, t, J=7.2 Hz), 7.22 (2H, d, J=7.3 Hz), 6.76 (2H, d, J=7.3 Hz), 4.71 (2H, s), 4.58 (2H, s), 3.32 (1H, septet, J=6.6 Hz), 1.41 (6H, d, J=6.6 Hz); $^{13}$C NMR (CDCl$_3$, 100 MHz): δ 176.3, 159.1, 157.8, 135.8 (2C), 133.7, 131.2, 128.5 (2C), 128.1 (2C), 127.8, 114.8 (2C), 109.4, 64.9, 59.4, 27.1, 20.7 (2C).

Example 5A. Preparation of 4-((3-(2,6-dichlorophenyl)-5-isopropylisoxazol-4-yl)methoxy)benzoic Acid (BAR2105)

Purification by silica gel (100% CH$_2$Cl$_2$) after step c, gave BAR2105 (quantitative yield). An analytic sample was obtained by HPLC on a Nucleodur 100-5 C18 (5 μm; 4.6 mm i.d.×250 mm), with MeOH/H$_2$O (75:25) as eluent (flow rate 1 mL/min) ($t_R$=9.2 min).

BAR2105 C$_{20}$H$_{17}$Cl$_2$NO$_4$ $^1$H NMR (CDCl$_3$, 400 MHz): δ 7.94 (2H, d, J=6.5 Hz), 7.37 (2H, d, J=7.0 Hz), 7.29 (1H, t, J=7.0 Hz), 6.77 (2H, d, J=6.5 Hz), 4.77 (2H, s), 3.31 (1H, septet, J=6.4 Hz), 1.41 (6H, d, J=6.4 Hz);

$^{13}$C NMR (CDCl$_3$, 100 MHz): δ 177.4, 162.4, 162.3, 158.9, 135.7 (2C), 132.2 (2C), 131.3, 128.0 (2C), 127.7, 123.0, 114.2 (2C), 108.8, 59.4, 27.1, 20.8 (2C).

Example 6A. Preparation of 3-(2,6-dichlorophenyl)-5-isopropyl-4-((4-(methylsulfonyl)phenoxy)methyl)isoxazole (BAR2116)

Purification by silica gel (100% CH$_2$Cl$_2$) after step a, gave BAR2116 (67%). An analytic sample was obtained by HPLC on a Nucleodur 100-5 C18 (5 μm; 4.6 mm i.d.×250 mm), with MeOH/H$_2$O (75:25) as eluent (flow rate 1 mL/min) ($t_R$=13.5 min).

BAR2116 C$_{20}$H$_{19}$Cl$_2$NO$_4$S $^1$H NMR (CDCl$_3$, 400 MHz): δ 7.79 (2H, d, J=8.5 Hz), 7.40 (2H, d, J=7.8 Hz), 7.32 (1H, t, J=7.8 Hz), 6.88 (2H, d, J=8.5 Hz), 4.80 (2H, s), 3.32 (1H, septet, J=6.9 Hz), 3.0 (3H, s), 1.43 (6H, d, J=6.9 Hz); $^{13}$C NMR (CDCl$_3$, 100 MHz): δ 176.6, 162.1, 158.9, 135.7 (2C), 132.8, 131.48, 129.5 (2C), 128.1 (2C), 127.5, 114.9 (2C), 108.5, 59.7, 44.2, 27.1, 20.8 (2C).

Example 7A. Preparation of methyl 3-((3-(2,6-dichlorophenyl)-5-isopropylisoxazol-4-yl)methoxy) benzoate (BAR2110)

Purification by silica gel (8:2 hexane/AcOEt and 0.5% TEA), after step a, gave BAR2110 (57%). An analytic sample was obtained by HPLC on a Nucleodur 100-5 C18 (5 μm; 4.6 mm i.d.×250 mm), with MeOH/H$_2$O (82:18) as eluent (flow rate 1 mL/min) ($t_R$=16.5 min).

BAR2110 C$_{21}$H$_{19}$Cl$_2$NO$_4$ $^1$H NMR (CDCl$_3$, 400 MHz): δ 7.60 (1H, d, J=7.8 Hz), 7.43 (1H, s), 7.38 (2H, d, J=7.7 Hz), 7.32-7.25 (2H, m, ovl), 6.94 (1H, d, J=8.3 Hz), 4.77 (2H, s), 3.89 (3H, s), 3.33 (1H, septet, J=6.9 Hz), 1.42 (6H, d, J=6.9 Hz);

$^{13}$C NMR (CDCl$_3$, 100 MHz): δ 176.4, 166.7, 159.1, 158.1, 135.7 (2C), 131.4, 131.2, 129.4, 128.1 (2C), 127.8, 122.5, 120.3, 114.6, 109.1, 59.5, 52.1, 27.1, 20.8 (2C).

Example 8A. Preparation of 3-((3-(2,6-dichlorophenyl)-5-isopropylisoxazol-4-yl)methoxy)benzonitrile (BAR2113)

Purification by silica gel (9:1 hexane/AcOEt and 0.5% TEA), after step a, gave BAR2113 (73%). An analytic sample was obtained by HPLC on a Nucleodur 100-5 C18 (5 μm; 4.6 mm i.d.×250 mm), with MeOH/H$_2$O (82:18) as eluent (flow rate 1 mL/min) ($t_R$=11.4 min).

BAR2113 C$_{20}$H$_{16}$Cl$_2$N$_2$O$_2$ $^1$H NMR (CDCl$_3$, 400 MHz): δ 7.40 (1H, s), 7.39 (2H, d, J=7.8 Hz), 7.33 (1H, dd, ovl), 7.31 (1H, t, ovl), 7.21 (1H, d, J=7.7 Hz), 6.99 (1H, d, J=8.0 Hz), 4.75 (2H, s), 3.31 (1H, septet, J=6.8 Hz), 1.41 (6H, d, J=6.8 Hz); $^{13}$C NMR (CDCl$_3$, 100 MHz): δ 176.6, 158.9, 158.1, 135.7 (2C), 131.4, 130.4, 128.1 (2C), 127.6, 125.0, 120.0, 118.4, 117.5, 113.2, 108.6, 59.6, 27.1, 20.8 (2C).

Example 9A. Preparation of (3-((3-(2,6-dichlorophenyl)-5-isopropylisoxazol-4-yl)methoxy)phenyl) methanol (BAR2112)

Purification after step b, by HPLC on a Nucleodur 100-5 C18 (5 μm; 4.6 mm i.d.×250 mm), with MeOH/H$_2$O (75:25) as eluent (flow rate 1 mL/min) ($t_R$=18 min) gave BAR2112 (quantitative yield).

BAR2112 C$_{20}$H$_{19}$Cl$_2$NO$_3$ $^1$H NMR (CDCl$_3$, 400 MHz): δ 7.39 (2H, d, J=7.5 Hz), 7.30 (1H, t, J=7.5 Hz), 7.19 (1H, t, J=7.8 Hz), 6.90 (1H, d, J=7.8 Hz), 6.80 (1H, s), 6.70 (1H, d, J=7.8 Hz), 4.73 (2H, s), 4.61 (2H, d, J=4.1 Hz), 3.33 (1H, septet, J=6.9 Hz), 1.41 (6H, d, J=6.9 Hz);

$^{13}$C NMR (CDCl$_3$, 100 MHz): δ 176.5, 159.0, 158.5, 142.5, 135.8 (2C), 131.2, 129.5, 128.1 (2C), 127.8, 119.6, 114.1, 112.8, 109.4, 65.0, 59.2, 27.1, 20.8 (2C).

Example 10A. Preparation of 3-((3-(2,6-dichlorophenyl)-5-isopropylisoxazol-4-yl)methoxy)benzoic Acid (BAR2111)

Purification after step c, by HPLC on a Nucleodur 100-5 C18 (5 μm; 4.6 mm i.d.×250 mm), with MeOH/H$_2$O (75:25) as eluent (flow rate 1 mL/min) ($t_R$=22.5 min) gave BAR2111 (89%).

BAR2111 C$_{20}$H$_{17}$Cl$_2$NO$_4$ $^1$H NMR (CDCl$_3$, 400 MHz): δ 7.65 (1H, d, J=7.0 Hz), 7.47 (1H, s), 7.37 (2H, d, J=7.5 Hz), 7.31-7.25 (2H, m, ovl), 6.97 (1H, d, J=7.8 Hz), 4.77 (2H, s), 3.32 (1H, septet, J=7.1 Hz), 1.41 (6H, d, J=7.1 Hz);

$^{13}$C NMR (CDCl$_3$, 100 MHz): δ 176.41, 159.7, 159.1, 158.2, 135.7 (2C), 131.3, 129.5 (2C), 128.0 (2C), 127.6, 123.2, 121.0, 115.2, 109.1, 59.5, 27.1, 20.8 (2C).

Example 11A. Preparation of Methyl 4'-((3-(2,6-dichlorophenyl)-5-isopropylisoxazol-4-yl)methoxy)-[1,1'-biphenyl]-3-carboxylate (BAR2118)

Purification by silica gel (100% CH$_2$Cl$_2$) after step a, gave BAR2118 (68%). An analytic sample was obtained by HPLC on a Nucleodur 100-5 C18 (5 μm; 4.6 mm i.d.×250 mm), with MeOH/H$_2$O (90:10) as eluent (flow rate 1 mL/min) ($t_R$=9.9 min).

BAR2118 C$_{27}$H$_{23}$Cl$_2$NO$_4$ $^1$H NMR (CDCl$_3$, 400 MHz): δ 8.20 (1H, s), 7.98 (1H, d, J=7.7 Hz), 7.71 (1H, d, J=7.7 Hz), 7.49 (2H, d, J=8.5 Hz), 7.48 (1H, t, J=7.7 Hz), 7.42 (2H, d, J=8.0 Hz), 7.33 (1H, dd, J=7.1, 8.0 Hz), 6.87 (2H, d, J=8.5 Hz), 4.78 (2H, s), 3.95 (3H, s), 3.36 (1H, septet, J=7.1 Hz), 1.44 (6H, d, J=7.1 Hz);

$^{13}$C NMR (CDCl$_3$, 100 MHz): δ 176.4, 167.1, 159.1, 158.1, 140.8, 135.8 (2C), 133.2, 131.2, 131.0, 130.6, 128.8, 127.8, 127.7, 128.1 (4C), 126.8, 115.1 (2C), 109.3, 59.4, 52.1, 27.1, 20.8 (2C).

Example 12A. Preparation of (4'-((3-(2,6-dichlorophenyl)-5-isopropylisoxazol-4-yl)methoxy)-[1,1'-biphenyl]-3-yl)methanol (BAR2120)

Purification by silica gel (9:1 hexane/AcOEt and 0.5% TEA) after step b, gave BAR2120 (83%). An analytic sample was obtained by HPLC on a Nucleodur 100-5 C18 (5 μm; 4.6 mm i.d.×250 mm), with MeOH/H$_2$O (83:17) as eluent (flow rate 1 mL/min) ($t_R$=8.5 min).

BAR2120 C$_{26}$H$_{23}$Cl$_2$NO$_3$ $^1$H NMR (CD$_3$OD, 400 MHz): δ 7.53 (1H, s), 7.52 (2H, d, J 7.5 Hz), 7.47 (1H, t ovl), 7.46 (2H, d, J=8.8 Hz), 7.43 (1H, d, J=7.8 Hz), 7.36 (1H, t, J=7.8 Hz), 7.27 (1H, d, J=7.8 Hz), 6.84 (2H, d, J=8.8 Hz), 4.84 (2H, s), 4.64 (2H, s), 3.43 (1H, septet, J=6.7 Hz), 1.42 (6H, d, J=6.7 Hz);

$^{13}$C NMR (CDCl$_3$, 100 MHz): δ 176.4, 157.8, 154.1, 141.4, 137.4, 135.8 (2C), 134.0, 131.2, 129.0, 128.1 (4C), 126.0, 125.4, 125.3, 122.8, 115.1 (2C), 109.3, 65.4, 59.4, 27.0, 20.8 (2C).

Example 13A. Preparation of 4'-((3-(2,6-dichlorophenyl)-5-isopropylisoxazol-4-yl)methoxy)-[1,1'-biphenyl]-3-carboxylic Acid (BAR2119)

Purification by silica gel (99:1 CH$_2$Cl$_2$/MeOH) after step c, gave BAR2119 (64%). An analytic sample was obtained by HPLC on a Nucleodur 100-5 C18 (5 μm; 4.6 mm i.d.×250 mm), with MeOH/H$_2$O (83:17) as eluent (flow rate 1 mL/min) ($t_R$=12.5 min).

BAR2119 C$_{26}$H$_{21}$Cl$_2$NO$_4$ $^1$H NMR (CDCl$_3$, 400 MHz): δ 8.27 (1H, s), 8.04 (1H, d, J=8.0 Hz), 7.76 (1H, d, J=7.7 Hz), 7.51 (2H, d, J=8.2 Hz), 7.50 (1H, t, J=8.0 Hz), 7.42 (2H, d, J=7.6 Hz), 7.33 (1H, t, J=7.6 Hz), 6.87 (2H, d, J=8.2 Hz), 4.78 (2H, s), 3.36 (1H, septet, J=7.1 Hz), 1.44 (6H, d, J=7.1 Hz);

$^{13}$C NMR (CDCl$_3$, 100 MHz): δ 176.4, 164.9, 160.6, 158.1, 140.8, 135.8 (2C), 133.1, 132.1, 131.5, 131.2, 128.8, 128.3, 128.1 (4C), 127.8, 127.7, 115.1 (2C), 109.3, 59.4, 27.1, 20.8 (2C).

Example 2. Preparation of BAR2106-2109, BAR2121-2124, BAR2139, 2140, and BAR2147

BAR2104, prepared according to Scheme 1, was alkylated with six different phenols via Mitsunobu reaction to afford BAR2106, BAR2107, BAR2121, BAR2122, BAR2138, and BAR2144. LiBH$_4$ reduction and alkaline hydrolysis on the methyl esters BAR2106, BAR2122, BAR2138 and BAR2144 furnished the corresponding alcohols BAR2108, BAR2124, BAR2140, BAR2146 and the acids BAR2109, BAR2123, BAR2139 and BAR2147 respectively (Scheme 2).

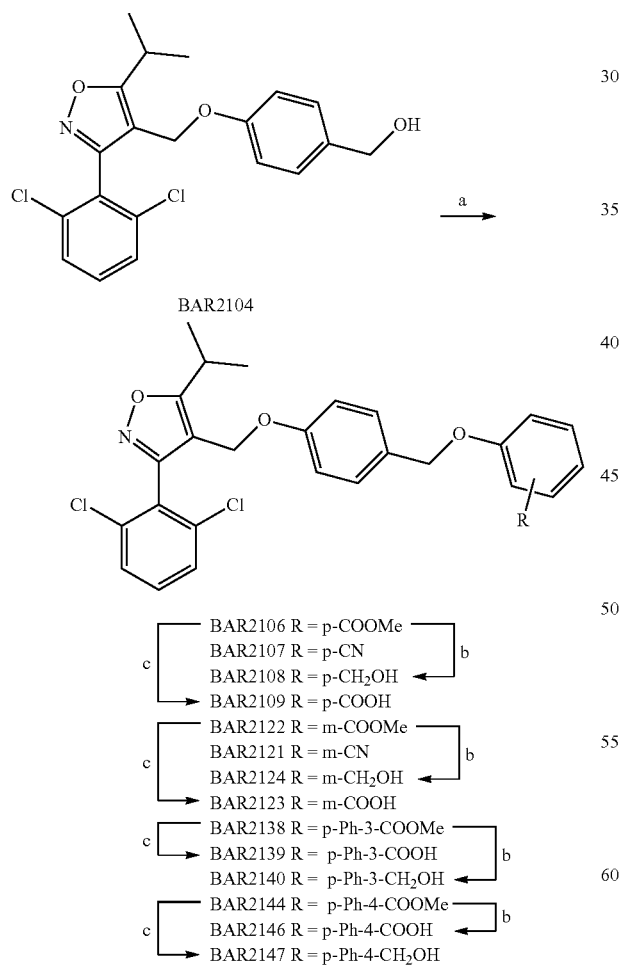

Scheme 2 a) PPh$_3$, DIAD, THF dry, 0° C.; b) LiBH$_4$, MeOH dry, THF dry, 0° C.; c) NaOH, MeOH:H$_2$O 1:1 v/v.

Example 2A. Preparation of Methyl 4-((4-((3-(2,6-dichlorophenyl)-5-isopropylisoxazol-4-yl)methoxy)benzyl)oxy)benzoate (BAR2106)

Purification by silica gel (100% CH$_2$Cl$_2$) after step a, gave BAR2106 (63%). An analytic sample of BAR2106 was obtained by HPLC on a Phenomenex C18 (5 μm; 4.6 mm i.d.×250 mm), with MeOH/H$_2$O (85:15) as eluent (flow rate 1 mL/min) (t$_R$=10.4 min).

BAR2106 C$_{28}$H$_{25}$Cl$_2$NO$_5$ $^1$H NMR (CDCl$_3$, 400 MHz): δ 7.98 (2H, d, J=8.0 Hz), 7.40 (2H, d, J=7.7 Hz), 7.33-7.26 (3H, m, ovl), 6.96 (2H, d, J=8.0 Hz), 6.79 (2H, d, J=7.7 Hz), 5.00 (2H, s), 4.72 (2H, s), 3.88 (3H, s), 3.32 (1H, septet, J=6.9 Hz), 1.41 (6H, d, J=6.9 Hz);

$^{13}$C NMR (CDCl$_3$, 100 MHz): δ 176.4, 166.8, 162.4, 159.1, 158.2, 135.7 (2C), 131.5, 131.2 (2C), 129.2 (2C), 128.8, 128.1 (2C), 127.3, 122.7, 114.9 (2C), 114.4 (2C), 109.3, 69.7, 59.4, 51.8, 27.1, 20.7 (2C).

Example 2B. Preparation of 4-((4-((3-(2,6-dichlorophenyl)-5-isopropylisoxazol-4-yl)methoxy)benzyl)oxy)benzonitrile (BAR2107)

Purification by silica gel (7:3 hexane/AcOEt and 0.5% TEA) after step a, gave BAR2107 (quantitative yield). An analytic sample was obtained by HPLC on a Phenomenex C18 5 μm (4.6 mm i.d.×250 mm), with MeOH/H$_2$O (87:13) as eluent (flow rate 1 mL/min) (t$_R$=8 min).

BAR2107 C$_{27}$H$_{22}$Cl$_2$N$_2$O$_3$ $^1$H NMR (CDCl$_3$, 400 MHz): δ 7.58 (2H, d, J=8.5 Hz), 7.40 (2H, d, J=8.0 Hz), 7.32 (1H, t, J=8.4 Hz), 7.27 (2H, d, J=8.4 Hz), 6.98 (2H, d, J=8.5 Hz), 6.80 (2H, d, J=8.0 Hz), 5.00 (2H, s), 4.73 (2H, s), 3.32 (1H, septet, J=6.9 Hz), 1.42 (6H, d, J=6.9 Hz);

$^{13}$C NMR (CDCl$_3$, 100 MHz): δ 176.1, 161.7, 158.8, 158.1, 135.5 (2C), 133.7 (2C), 131.1, 129.0 (2C), 128.1, 127.8 (2C), 127.5, 118.9, 115.3 (2C), 114.7 (2C), 109.1, 103.8, 69.7, 59.2, 26.8, 20.5 (2C).

Example 2C. Preparation of (4-((4-((3-(2,6-dichlorophenyl)-5-isopropylisoxazol-4-yl)methoxy)benzyl)oxy)phenyl)methanol (BAR2108)

Purification after step b, by HPLC on a Phenomenex C18 (5 μm, 4.6 mm i.d.×250 mm), with MeOH/H$_2$O (75:25) as eluent (flow rate 1 mL/min) (t$_R$=24 min) gave BAR2108 (quantitative yield).

BAR2108 C$_{27}$H$_{25}$Cl$_2$NO$_4$ $^1$H NMR (CDCl$_3$, 400 MHz): δ 7.39 (2H, d, J=7.9 Hz), 7.31 (1H, ovl), 7.28 (4H, d, ovl), 6.94 (2H, d, J=8.3 Hz), 6.80 (2H, d, J=8.3 Hz), 4.96 (2H, s), 4.72 (2H, s), 4.62 (2H, d, J=5.1 Hz), 3.33 (1H, septet, J=6.9 Hz), 1.41 (6H, d, J=6.9 Hz);

$^{13}$C NMR (CDCl$_3$, 100 MHz): δ 176.5, 159.3, 158.4, 158.2, 135.7 (2C), 133.7, 131.4, 129.8 (2C), 129.2 (2C), 128.8, 128.2 (2C), 128.0, 115.0 (4C), 109.5, 69.8, 64.9, 59.6, 27.3, 20.9 (2C).

Example 2D. Preparation of 4-((4-((3-(2,6-dichlorophenyl)-5-isopropylisoxazol-4-yl)methoxy)benzyl)oxy)benzoic Acid (BAR2109)

Purification by silica gel (7:3 hexane:AcOEt) after step c, gave BAR2109 (93%). An analytic sample was obtained by HPLC on a Nucleodur VP 100-5 Silica (5 µm; 10 mm i.d.×250 mm), with n-hexane/AcOEt (50:50) as eluent (flow rate 3 mL/min) ($t_R$=15 min).

BAR2109 $C_{27}H_{23}Cl_2NO_5$ $^1$H NMR (CDCl$_3$, 400 MHz): δ 8.05 (2H, d, J=8.6 Hz), 7.40 (2H, d, J=7.89 Hz), 7.33-7.29 (3H, m, ovl), 6.99 (2H, d, J=8.6 Hz), 6.81 (2H, d, J=8.4 Hz), 5.03 (2H, s), 4.73 (2H, s), 3.32 (1H, septet, J=6.9 Hz), 1.42 (6H, d, J=6.9 Hz);

$^{13}$C NMR (CDCl$_3$, 100 MHz): δ 176.4, 163.2, 162.4, 158.9, 158.3, 135.8 (2C), 132.3, 131.2 (2C), 129.2 (2C), 128.7, 128.1 (2C), 127.8, 121.7, 114.9 (2C), 114.5 (2C), 109.3, 69.8, 59.4, 27.1, 20.8 (2C).

Example 2E. Preparation of Methyl 3-((4-((3-(2,6-dichlorophenyl)-5-isopropylisoxazol-4-yl)methoxy)benzyl)oxy)benzoate (BAR2122)

Purification by silica gel (100% CH$_2$Cl$_2$) after step a, gave BAR2122 (61%). An analytic sample was obtained by HPLC on a Nucleodur 100-5 C18 (5 µm; 4.6 mm i.d.×250 mm), with MeOH/H$_2$O (85:15) as eluent (flow rate 1 mL/min) ($t_R$=18 min).

BAR2122 $C_{28}H_{25}Cl_2NO_5$ $^1$H NMR (CDCl$_3$, 400 MHz): δ 7.63 (2H, d, J=7.6 Hz), 7.40 (2H, d, J=8.1 Hz), 7.33 (1H, t, J=8.1 Hz), 7.30-7.29 (3H, m, ovl), 7.13 (1H, d, J=7.9 Hz), 6.79 (2H, d, J=8.3 Hz), 5.00 (2H, s), 4.72 (2H, s), 3.91 (3H, s), 3.32 (1H, septet, J=6.9 Hz), 1.41 (6H, d, J=6.9 Hz);

$^{13}$C NMR (CDCl$_3$, 100 MHz): δ 176.4, 171.1, 169.3, 157.0, 152.9, 135.8 (2C), 131.2, 129.4, 129.2 (4C), 128.1 (2C), 122.2, 120.8, 120.2, 115.0, 114.8 (2C), 109.3, 59.4, 52.2, 27.1, 20.7 (2C).

Example 2F. Preparation of 3-((4-((3-(2,6-dichlorophenyl)-5-isopropylisoxazol-4-yl)methoxy)benzyl)oxy)benzonitrile (BAR2121)

Purification by silica gel (100% CH$_2$Cl$_2$) after step a, gave BAR2121 (93%). An analytic sample was obtained by HPLC on a Nucleodur 100-5 C18 (5 µm; 4.6 mm i.d.×250 mm), with MeOH/H$_2$O (82:18) as eluent (flow rate 1 mL/min) ($t_R$=16 min).

BAR2121 $C_{27}H_{22}Cl_2N_2O_3$ $^1$H NMR (CDCl$_3$, 400 MHz): δ 7.40 (2H, d, J=7.8 Hz), 7.33 (1H, t, J=7.8 Hz), 7.29-7.23 (4H, m, ovl), 7.16 (2H, ovl), 6.79 (2H, d, J=8.5 Hz), 4.97 (2H, s), 4.72 (2H, s), 3.32 (1H, septet, J=7.0 Hz), 1.41 (6H, d, J=7.0 Hz);

$^{13}$C NMR (CDCl$_3$, 100 MHz): δ 176.4, 163.2, 159.1, 158.3, 135.7 (2C), 131.2, 130.4, 129.7, 129.1 (2C), 128.1 (2C), 124.7, 123.9, 120.5, 118.9, 118.7, 114.9, 114.8, 114.6, 109.3, 69.9, 59.4, 27.1, 20.8 (2C).

Example 2G. Preparation of (3-((4-((3-(2,6-dichlorophenyl)-5-isopropylisoxazol-4-yl)methoxy)benzyl)oxy)phenyl)methanol (BAR2124)

Purification after step b, by HPLC on a Phenomenex C18 5 µm (4.6 mm i.d.×250 mm), with MeOH/H$_2$O (80:20) as eluent (flow rate 1 mL/min) ($t_R$=10 min) gave BAR2124 (84%).

BAR2124 $C_{27}H_{25}Cl_2NO_4$ $^1$H NMR (CDCl$_3$, 400 MHz): δ 7.40 (2H, d, J=7.70 Hz), 7.33 (1H, t, J=7.70 Hz), 7.28 (2H, d, J=8.4 Hz), 7.27 (1H, dd, ovl), 6.98 (1H, d, J=7.5 Hz), 6.87 (1H, d, J=8.0 Hz), 6.78 (2H, d, J=8.4 Hz), 4.96 (2H, s), 4.72 (2H, s), 4.66 (2H, br s), 3.32 (1H, septet, J=6.9 Hz), 1.41 (6H, d, J=6.9 Hz);

$^{13}$C NMR (CDCl$_3$, 100 MHz): δ 176.3, 159.1, 158.9, 158.1, 142.5, 135.7 (2C), 131.2, 129.6, 129.0 (3C), 128.0 (2C), 123.2, 119.3, 114.8 (2C), 114.1, 113.2, 109.3, 69.6, 65.2, 59.3, 27.1, 20.8 (2C).

Example 2H. Preparation of 3-((4-((3-(2,6-dichlorophenyl)-5-isopropylisoxazol-4-yl)methoxy)benzyl)oxy)benzoic Acid (BAR2123)

Purification by silica gel (8:2 hexane/AcOEt) after step c, gave BAR2123 (72%). An analytic sample was obtained by HPLC on a Phenomenex C18 5 µm (4.6 mm i.d.×250 mm), with MeOH/H$_2$O (80:20) as eluent (flow rate 1 mL/min) ($t_R$=12 min).

BAR2123 $C_{27}H_{23}Cl_2NO_5$ $^1$H NMR (CD$_3$OD, 400 MHz): δ 7.58 (1H, s), 7.57 (1H, d, J 8.0 Hz), 7.49 (2H, d, J=7.7 Hz), 7.43 (1H, dd, J=8.0, 8.4 Hz), 7.30 (1H, t, J=7.7 Hz), 7.28 (2H, d, J=8.6 Hz), 7.10 (1H, d, J=8.4 Hz), 6.77 (2H, d, J=8.6 Hz), 5.00 (2H, s), 4.81 (2H, s), 3.41 (1H, septet, J=7.1 Hz), 1.40 (6H, d, J=7.1 Hz);

$^{13}$C NMR (CDCl$_3$, 100 MHz): δ 176.3, 169.7, 159.1, 158.6, 158.1, 135.7 (2C), 132.0 (2C), 131.2, 129.5, 129.2, 128.4, 128.0 (2C), 122.7, 120.8, 116.1, 115.3, 114.8 (2C), 109.3, 69.7, 59.3, 27.1, 20.7 (2C).

Example 2I. Preparation of 4'-((4-((3-(2,6-dichlorophenyl)-5-isopropylisoxazol-4-yl)methoxy)benzyl)oxy)-[1,1'-biphenyl]-3-carboxylic Acid (BAR2139)

Purification by HPLC on a Nucleodur Sphinx C18 5 µm (4.6 mm i.d.×250 mm), with MeOH/H$_2$O (95:5) and 0.1% TFA as eluent (flow rate 1 mL/min) gave BAR2139 ($t_R$=5 min).

BAR2139 $C_{33}H_{27}Cl_2NO_5$ $^1$H NMR (CDCl$_3$, 400 MHz): δ 8.27 (1H, br s) 8.02 (1H, d, J=7.7 Hz), 7.78 (1H, d, J=7.7 Hz), 7.56 (2H, d, J=8.2 Hz), 7.52 (1H, t, J=7.7 Hz), 7.40 (2H, d, J=7.9 Hz), 7.32 (2H, d, J=8.2 Hz), 7.30 (1H, t, J=7.9 Hz), 6.81 (2H, d, J=8.2 Hz), 5.01 (2H, s), 4.73 (2H, s), 3.33 (1H, septet, J=7.0 Hz), 1.42 (6H, d, J=7.0 Hz);

$^{13}$C NMR (CDCl$_3$, 100 MHz): δ 176.3, 165.3, 159.1, 158.7, 158.2, 141.1, 135.8 (2C), 132.6, 131.8, 131.3, 129.5 (2C), 129.2 (2C), 128.9, 128.4 (2C), 128.2 (2C), 128.1, 127.8, 115.3 (2C), 114.9 (2C), 109.3, 69.6, 59.6, 27.0, 20.7 (2C).

Example 2J. Preparation of (4'-((4-((3-(2,6-dichlorophenyl)-5-isopropylisoxazol-4-yl)methoxy)benzyl)oxy)-[1,1'-biphenyl]-3-yl)methanol (BAR2140)

Purification by HPLC on a Nucleodur Sphinx C18 5 µm (4.6 mm i.d.×250 mm), with MeOH/H$_2$O (85:15) as eluent (flow rate 1 mL/min) gave BAR2140 ($t_R$=12 min).

BAR2140 $C_{33}H_{29}Cl_2NO_4$ $^1$H NMR (CDCl$_3$, 400 MHz): δ 7.54-7.39 (9H, ovl), 7.27 (2H, d, J=7.8 Hz), 7.01, (2H, d, J=7.9 Hz), 6.76 (2H, d, J=8.0 Hz), 4.98 (2H, s), 4.79 (2H, s), 4.64 (2H, s), 3.39 (1H, septet, J=7.0 Hz), 1.38 (6H, d, J=7.0 Hz);

$^{13}$C NMR (CDCl$_3$, 100 MHz): δ 176.4, 159.1, 158.4, 158.2, 141.3, 141.2, 135.8 (2C), 133.7, 131.2, 129.6, 129.2, 129.0, 128.2 (2C), 128.1 (2C), 127.8 (2C), 126.1, 125.4, 125.3, 115.1 (2C), 114.8 (2C), 109.4, 69.6, 65.3, 59.3, 27.0, 20.8 (2C).

Example 2K. Preparation of 4'-((4-((3-(2,6-dichlorophenyl)-5-isopropylisoxazol-4-yl)methoxy)benzyl)oxy)-[1,1'-biphenyl]-4-carboxylic Acid (BAR2147)

Purification by HPLC on a Nucleodur Sphinx C18 5 µm (4.6 mm i.d.×250 mm), with MeOH/H$_2$O (90:10) as eluent (flow rate 1 mL/min) ($t_R$=8 min).

BAR2147 C$_{33}$H$_{27}$Cl$_2$NO$_5$ $^1$H NMR (CDCl$_3$, 400 MHz): δ 7.8 (2H, d, J=8.6 Hz), 7.6 (2H, d, J=8.6 Hz), 7.53 (2H, d, J=8.5 Hz), 7.40 (2H, d, J=7.9 Hz), 7.32 (3H, ovl), 7.05 (2H, d, J=8.5 Hz), 6.81 (2H, d, J=8.2 Hz), 5.01 (2H, s), 4.73 (2H, s), 3.33 (1H, septet, J=7.0 Hz), 1.42 (6H, d, J=7.0 Hz);

$^{13}$C NMR (CDCl$_3$, 100 MHz): δ 176.3, 169.3, 159.4, 159.1, 158.2, 145.1, 135.8 (2C), 132.6 (2C), 131.7, 131.3, 129.3, 129.1 (2C), 128.4 (2C), 128.2 (2C), 127.8, 127.1 (2C), 115.4 (2C), 114.8 (2C), 109.3, 69.8, 59.4, 27.1, 20.8 (2C).

Example 3. Preparation of BAR2151, BAR2159, BAR2175, BAR2183

Starting from alcohol BAR2112 and following the procedure previously described in example 2 (scheme 2), alkylation with four different phenols via Mitsunobu reaction and hydrolysis afforded carboxylic acids BAR2151, BAR2159, BAR2175, BAR2183.

Scheme 3

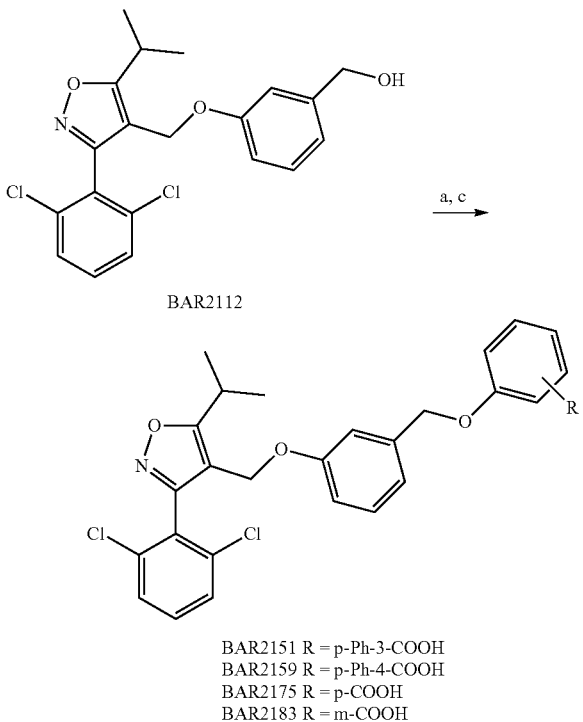

BAR2151 R = p-Ph-3-COOH
BAR2159 R = p-Ph-4-COOH
BAR2175 R = p-COOH
BAR2183 R = m-COOH a) PPh$_3$, DIAD, Phenols-COOCH$_3$, THF dry, 0° C.; c) NaOH, MeOH:H$_2$O 1:1 v/v.

Example 3A. Preparation of 4'-((3-((3-(2,6-dichlorophenyl)-5-isopropylisoxazol-4-yl)methoxy)benzyl)oxy)-[1,1'-biphenyl]-3-carboxylic Acid (BAR2151)

Purification by HPLC on a Phenomenex C18 5 µm (4.6 mm i.d.×250 mm), with MeOH/H$_2$O (80:20) as eluent (flow rate 1 mL/min) gave BAR2151 ($t_R$=11 min).

BAR2151 C$_{33}$H$_{27}$Cl$_2$NO$_5$ $^1$H NMR (CD$_3$OD, 400 MHz): δ 8.27 (1H, br s) 8.02 (1H, d, J=7.8 Hz), 7.75 (1H, d, J=7.8 Hz), 7.56 (2H, d, J=8.2 Hz), 7.52 (1H, t, J=7.8 Hz), 7.40 (2H, d, J=8.0 Hz), 7.32 (1H, t, J=8.0 Hz), 7.30 (1H, t, J=7.5 Hz), 7.04 (2H, d, J=8.2 Hz), 7.00 (1H, d, J=7.5 Hz), 6.85 (1H, s), 6.80 (1H, d, J=7.5 Hz), 5.06 (2H, s), 4.78 (2H, s), 3.33 (1H, septet, J=7.3 Hz), 1.42 (6H, d, J=7.3 Hz);

$^{13}$C NMR (CDCl$_3$, 100 MHz): δ 176.4, 165.5, 159.1, 158.7, 158.5, 141.0, 137.7, 135.6 (2C), 132.3, 131.8, 131.6, 131.4, 129.8, 129.5, 129.1, 128.9, 128.4 (2C), 128.2 (2C), 127.6, 120.4, 115.1 (2C), 114.5, 113.7, 109.3, 69.8, 59.3, 27.0, 20.7 (2C).

Example 3B. Preparation of 4'-((3-((3-(2,6-dichlorophenyl)-5-isopropylisoxazol-4-yl)methoxy)benzyl)oxy)-[1,1'-biphenyl]-4-carboxylic Acid (BAR2159)

Purification by HPLC on a Nucleodur Sphinx C18 5 µm (4.6 mm i.d.×250 mm), with MeOH/H$_2$O (90:10) as eluent (flow rate 1 mL/min) gave BAR2159 ($t_R$=8 min).

BAR2159 C$_{33}$H$_{27}$Cl$_2$NO$_5$ $^1$H NMR (CDCl$_3$, 400 MHz): δ 7.90 (2H, d, J=7.7 Hz), 7.70 (2H, d, J=7.7 Hz), 7.56 (2H, d, J=8.2 Hz), 7.53 (1H, t, J=8.0 Hz), 7.40 (2H, d, J=7.9 Hz), 7.30 (1H, t, J=7.9 Hz), 7.05 (2H, d, J=8.2 Hz), 7.02 (1H, d, J=8.0 Hz), 6.88 (1H, s), 6.76 (1H, d, J=8.0 Hz), 5.03 (2H, s), 4.73 (2H, s), 3.33 (1H, septet, J=7.0 Hz), 1.42 (6H, d, J=7.0 Hz);

$^{13}$C NMR (CDCl$_3$, 100 MHz): δ 176.3, 165.3, 159.3, 159.1, 158.2, 141.1, 137.7, 135.8 (2C), 132.6, 131.5, 131.2, 129.5, 129.2 (2C), 129.1, 128.1 (2C), 128.0 (2C), 123.8 (2C), 115.4 (2C), 120.0, 114.5, 113.7, 109.3, 69.8, 59.4, 27.0, 20.7 (2C).

Example 3C. Preparation of 4-(3-((3-(2,6-dichlorophenyl)-5-isopropylisoxazol-4-yl)methoxy)benzyl)oxy)benzoic Acid (BAR2175)

Purification by HPLC on a Nucleodur Sphinx C18 5 µm (4.6 mm i.d.×250 mm), with MeOH/H$_2$O (80:20) as eluent (flow rate 1 mL/min) gave BAR2175 ($t_R$=13 min).

BAR2175 C$_{27}$H$_{23}$Cl$_2$NO$_5$ $^1$H NMR (CDCl$_3$, 400 MHz): δ 8.05 (2H, d, J=8.7 Hz), 7.40 (2H, d, J=7.9 Hz), 7.32 (1H, t, J=7.9 Hz), 7.29 (1H, d, J=8.0 Hz), 7.25 (1H, t ovl), 7.0 (2H, d, J=8.7 Hz), 6.85 (1H, s), 6.76 (1H, d, J=8.0 Hz), 5.07 (2H, s), 4.74 (2H, s), 3.33 (1H, septet, J=7.0 Hz), 1.44 (6H, d, J=7.0 Hz);

$^{13}$C NMR (CDCl$_3$, 100 MHz): δ 176.4, 163.9, 159.3, 159.0, 158.5, 137.8, 135.8 (2C), 132.3 (2C), 131.5, 131.3, 129.7, 129.5, 128.0 (2C), 120.2, 114.6, 114.4 (2C), 113.6, 109.2, 69.9, 59.3, 27.0, 20.7 (2C).

Example 3D. Preparation of 3-((3-((3-(2,6-dichlorophenyl)-5-isopropylisoxazol-4-yl)methoxy)benzyl)oxy)benzoic Acid (BAR2183)

Purification by HPLC on a Nucleodur Sphinx C18 5 µm (4.6 mm i.d.×250 mm), with MeOH/H$_2$O (80:20) as eluent (flow rate 1 mL/min) gave BAR2183 ($t_R$=15 min).

BAR2183 C$_{27}$H$_{23}$Cl$_2$NO$_5$ $^1$H NMR (CDCl$_3$, 400 MHz): δ 7.72 (1H, d, J=7.5 Hz), 7.67 (1H, br s), 7.41 (1H, ovl), 7.40 (2H, d, ovl), 7.31 (1H, t, ovl), 7.30 (1H, tovl), 7.24 (1H, d, J=8.0 Hz), 7.20 (1H, d, J=8.2 Hz), 6.87 (1H, br s), 6.76 (1H, d, J=8.3 Hz), 5.04 (2H, s), 4.75 (2H, s), 3.34 (1H, septet, J=6.9 Hz), 1.42 (6H, d, J=6.9 Hz);

$^{13}$C NMR (CDCl$_3$, 100 MHz): δ 176.7, 165.3, 159.0, 158.9, 158.5, 137.7, 135.7 (2C), 131.3, 129.6, 129.3, 128.9, 128.4, 128.2 (2C), 120.9, 120.5, 116.1, 115.3, 114.7, 113.8, 110.1, 69.6, 59.3, 27.0, 20.5 (2C).

Example 4. Preparation of BAR2163, BAR2171, BAR2199, BAR2207

Starting from alcohol BAR2120 and following the procedure previously described in example 2 and 3 (scheme 2 or scheme 3), alkylation with two different phenols and alkaline hydrolysis afforded carboxylic acids BAR2163, BAR2171, BAR2199 and BAR2207 (scheme 4).

Scheme 4

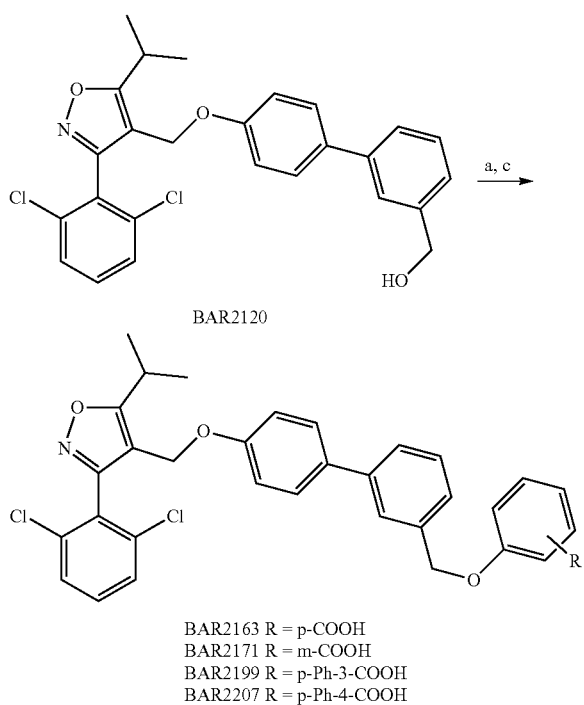

BAR2120

BAR2163 R = p-COOH
BAR2171 R = m-COOH
BAR2199 R = p-Ph-3-COOH
BAR2207 R = p-Ph-4-COOH a) PPh$_3$, DIAD, Phenols-COOCH$_3$ THF dry, 0° C.; c) NaOH, MeOH:H$_2$O 1:1 v/v.

Example 4A. Preparation of 4-((4'-((3-(2,6-dichlorophenyl)-5-isopropylisoxazol-4-yl)methoxy)-[1,1'-biphenyl]-3-yl)methoxy)benzoic Acid (BAR2163)

Purification by HPLC on a Luna polar C18 5 μm (4.6 mm i.d.×250 mm), with MeOH/H$_2$O (85:15) as eluent (flow rate 1 mL/min) gave BAR2163 (t$_R$=13 min).
BAR2163 C$_{33}$H$_{27}$Cl$_2$NO$_5$
$^1$H NMR (CDCl$_3$, 400 MHz): δ 7.60 (2H, d, J=8.8 Hz), 7.55, (1H, br s), 7.51 (1H, d, J=7.9 Hz), 7.46 (2H, d, J=8.5 Hz), 7.42 (2H, d, J=7.9 Hz), 7.40 (1H, t, ovl), 7.35 (1H, d, J=7.5 Hz), 7.33 (1H, t, J=7.9 Hz), 7.04 (1H, d, J=8.8 Hz), 6.87 (2H, d, J=8.5 Hz), 5.16 (2H, s), 4.77 (2H, s), 3.36 (1H, septet, J=7.0 Hz), 1.44 (6H, d, J=7.2 Hz);
$^{13}$C NMR (CDCl$_3$, 100 MHz): δ 176.4, 165.3, 160.0, 159.1, 157.9, 141.3, 136.2, 135.8 (2C), 134.0, 133.7, 131.1 (3C), 129.2, 128.2 (2C), 128.1 (2C), 127.8, 126.7, 125.8 (2C), 115.6 (2C), 115.0 (2C), 109.3, 70.3, 59.3, 27.1, 20.7 (2C).

Example 4B. Preparation of 3-((4'-((3-(2,6-dichlorophenyl)-5-isopropylisoxazol-4-yl)methoxy)-[1,1'-biphenyl]-3-yl)methoxy)benzoic Acid (BAR2171)

Purification by HPLC on a Luna Polar C18 5 μm (4.6 mm i.d.×250 mm), with MeOH/H$_2$O (85:15) as eluent (flow rate 1 mL/min) gave BAR2171 (t$_R$=20 min).
BAR2171 C$_{33}$H$_{27}$Cl$_2$NO$_5$
$^1$H NMR (CDCl$_3$, 400 MHz): δ 7.51 (1H, br s), 7.51-7.22 (12H, ovl) 6.87 (2H, d, J=8.4 Hz), 5.10 (2H, s), 4.78 (2H, s), 3.36 (1H, septet, J=7.3 Hz), 1.44 (6H, d, J=7.3 Hz);
$^{13}$C NMR (CDCl$_3$, 100 MHz): δ 176.5, 165.3, 159.1, 158.7, 157.9, 141.2, 136.3, 135.8 (2C), 133.8, 131.2, 130.4, 129.2, 128.2 (2C), 128.1 (2C), 126.7, 125.8 (2C), 124.8, 120.5, 118.7, 117.8, 115.1 (2C), 113.3, 109.4, 70.4, 59.5, 27.0, 20.7 (2C).

Example 4C. Preparation of 3-((4'-((3-(2,6-dichlorophenyl)-5-isopropylisoxazol-4-yl)methoxy)-[1,1'-biphenyl]-4-yl)methoxy)benzoic Acid (BAR2199)

Purification by HPLC Luna Polar C18 5 μm (4.6 mm i.d.×250 mm), with MeOH/H$_2$O (85:15) as eluent (flow rate 1 mL/min) gave BAR2199 (t$_R$=23 min).
BAR2199 C$_{33}$H$_{27}$Cl$_2$NO$_5$
$^1$H NMR (CDCl$_3$, 400 MHz): δ 7.57 (1H, br s), 7.22-7.51 (12H, ovl), 6.87 (2H, d, J=8.1 Hz), 5.16 (2H, s), 5.00 (2H, s), 3.33 (1H, septet, J=7.0 Hz), 1.44 (6H, d, J=7.0 Hz);
$^{13}$C NMR (CDCl$_3$, 100 MHz): δ 176.5, 169.3, 160.1, 159.3, 158.1, 141.0, 135.8 (2C), 135.6, 133.0, 131.2 (2C), 130.5 (2C), 130.1 (2C), 129.6, 128.7, 128.2 (2C), 128.1 (2C), 122.6, 119.5, 114.9 (2C), 114.4, 109.3, 70.6, 59.8, 27.0, 20.7 (2C).

Example 4D. Preparation of 4-((4'-((3-(2,6-dichlorophenyl)-5-isopropylisoxazol-4-yl)methoxy)-[1,1'-biphenyl]-4-yl)methoxy)benzoic Acid (BAR2207)

Purification by HPLC on a Luna Polar C18 5 μm (4.6 mm i.d.×250 mm), with MeOH/H$_2$O (85:15) as eluent (flow rate 1 mL/min) gave BAR2207 (t$_R$=15 min).
BAR2207 C$_{33}$H$_{27}$Cl$_2$NO$_5$
$^1$H NMR (CDCl$_3$, 400 MHz): δ 8.02 (2H, d, J=8.2 Hz), 7.61 (2H, d, J=8.0 Hz), 7.47 (2H, d, J=7.7 Hz), 7.40 (2H, d, J=7.9 Hz), 7.39 (2H, d, J=7.7 Hz), 7.32 (1H, t, J=7.9 Hz), 7.03 (2H, d, J=8.0 Hz), 6.90 (2H, d, J=8.2 Hz), 5.20 (2H, s), 5.05 (2H, s), 3.33 (1H, septet, J=7.0 Hz), 1.45 (6H, d, J=7.0 Hz);
$^{13}$C NMR (CDCl$_3$, 100 MHz): δ 176.3, 165.5, 159.1, 158.7, 158.5, 141.1, 135.8 (2C), 133.0, 132.6, 131.7, 131.3 (2C), 131.2, 129.2 (2C), 129.1 (2C), 128.9, 128.2 (2C), 128.0 (2C), 115.4 (2C), 114.9 (2C), 109.3, 70.5, 59.3, 27.0, 20.7 (2C).

Example 5. Preparation of BAR2222-BAR2226, BAR2227, and BAR2228

Following the same procedure previously described for the synthesis of the carboxylic acid BAR2119 (scheme 1 and example 12A), and changing alternatively the starting material (different aldehydes) or different β-ketoesters for isoxazole formation, BAR2222-BAR2226, BAR2227 and BAR2228, respectively, were synthesized.

Example 5A. Preparation of 4'-((3-(2-chlorophenyl)-5-isopropylisoxazol-4-yl)methoxy)-[1,1'-biphenyl]-3-carboxylic Acid (BAR2222)

Purification by HPLC on a Nucleodur Sphinx RP C18 column (5 μm; 4.6 mm i.d.×250 mm) with MeOH/$H_2O$ (80:20) as eluent (flow rate 1 mL/min), furnished pure BAR2222 ($t_R$=13.1 min).

BAR2222 $C_{26}H_{22}ClNO_4$ $^1$H NMR (CDCl$_3$, 400 MHz): δ 8.27 (1H, br s) 8.04 (1H, d, J=7.32 Hz), 7.75 (1H, d, J=7.32 Hz), 7.48-7.51 (5H, m, ovl), 7.42 (1H, t, J=7.41 Hz), 7.35 (1H, t, J=7.41 Hz), 6.86 (2H, d, J=8.05 Hz), 4.84 (2H, s), 3.35 (1H, septet, J=6.93 Hz), 1.44 (6H, d, J=6.93 Hz).

$^{13}$C NMR (CDCl$_3$, 100 MHz): δ 176.5 (2C), 161.1, 157.6, 140.0, 133.3, 133.1, 131.7, 131.6, 130.9, 130.8, 129.7, 129.6, 128.2, 128.1 (2C), 127.9, 127.8, 126.8, 114.8 (2C), 109.2, 59.4, 26.9, 20.6 (2C).

Example 5B. Preparation of 4'-((3-(2-bromophenyl)-5-isopropylisoxazol-4-yl)methoxy)-[1,1'-biphenyl]-3-carboxylic Acid (BAR2223)

Purification by HPLC on a Nucleodur Sphinx RP C18 column (5 μm; 4.6 mm i.d.×250 mm) with MeOH/$H_2O$ (80:20) as eluent (flow rate 1 mL/min), furnished pure BAR2223 ($t_R$=12.6 min).

BAR2223 $C_{26}H_{22}BrNO_4$ $^1$H NMR (CDCl$_3$, 400 MHz): δ 8.26 (1H, br s) 8.04 (1H, d, J 7.85 Hz), 7.77 (1H, d, J=7.85 Hz), 7.64 (1H, d, J=8.20 Hz), 7.53 (1H, t, J=7.85 Hz), 7.51 (1H, t, ovl), 7.51 (2H, d, J=8.61 Hz), 7.18 (1H, t, J=8.20 Hz), 6.88 (2H, d, J=8.61 Hz), 4.79 (2H, s), 3.37 (1H, septet, J=7.07 Hz), 1.45 (6H, d, J=7.07 Hz).

$^{13}$C NMR (CDCl$_3$, 100 MHz): δ 176.6, 171.4, 162.6, 157.8, 140.4, 133.6, 132.9, 131.8, 131.1, 130.4, 130.3, 128.5, 128.2, 128.13 (2C), 128.1, 127.4, 126.2, 123.0, 115.1 (2C), 109.2, 59.6, 27.0, 20.7 (2C).

Example 5C. Preparation of 4'-((5-isopropyl-3-(2-trifluoromethyl)phenyl)isoxazol-4-yl)methoxy)-[1,1'-biphenyl]-3-carboxylic Acid (BAR2224)

Purification by HPLC on a Nucleodur Sphinx RP C18 column (5 μm; 4.6 mm i.d.×250 mm) with MeOH/$H_2O$ (80:20) as eluent (flow rate 1 mL/min), furnished pure BAR2224 ($t_R$=10.8 min).

BAR2224 $C_{27}H_{22}F_3NO_4$ $^1$H NMR (CDCl$_3$, 400 MHz): δ 8.25 (1H, br s) 8.03 (1H, d, J=7.90 Hz), 7.81 (1H, d, J=7.66 Hz), 7.76 (1H, d, J=7.66 Hz), 7.61 (1H, m, ovl), 7.60 (1H, m, ovl), 7.52-7.51 (4H, ovl), 6.88 (2H, d, J=8.72 Hz), 4.72 (2H, s), 3.33 (1H, septet, J=7.03 Hz), 1.44 (6H, d, J=7.03 Hz).

$^{13}$C NMR (CDCl$_3$, 100 MHz): δ 176.4, 171.0, 161.3, 158.1, 140.9, 133.1, 132.0, 131.8, 131.5, 129.9, 129.8, 129.7, 128.9, 128.4, 128.3, 128.2 (2C), 126.5, 126.4, 122.2, 115.1 (2C), 109.4, 59.1, 27.0, 20.8 (2C).

Example 5D. Preparation of 4'-((3-(2-bromo-6-chlorophenyl)-5-isopropylisoxazol-4-yl)methoxy)-[1,1'-biphenyl]-3-carboxylic Acid (BAR2225)

Purification by HPLC on a Nucleodur Sphinx RP 018 column (5 μm; 4.6 mm i.d.×250 mm) with MeOH/$H_2O$ (80:20) as eluent (flow rate 1 mL/min), furnished pure BAR2225 ($t_R$=36.7 min).

BAR2225 $C_{26}H_{21}BrClNO_4$ $^1$H NMR (CDCl$_3$, 400 MHz): δ 8.23 (1H, br s) 8.00 (1H, d, J=7.77 Hz), 7.71 (1H, d, J=7.77 Hz), 7.58 (1H, d, J=7.77 Hz), 7.44-7.46 (4H, m, ovl), 7.23 (1H, t, J=8.55 Hz), 6.85 (2H, d, J=8.73 Hz), 4.76 (2H, br s), 3.35 (1H, septet, J=7.03 Hz), 1.43 (6H, d, J=7.03 Hz).

$^{13}$C NMR (CDCl$_3$, 100 MHz): δ 176.4, 171.7, 160.6, 158.2, 140.9, 135.7, 133.0, 131.8, 131.6, 131.2, 129.7, 128.9, 128.6, 128.4, 128.3 (2C), 128.1 (2C), 125.0, 115.2 (2C), 109.1, 59.4, 27.0, 20.7 (2C).

Example 5E. Preparation of 4'-((3-(2,6-dibromophenyl)-5-isopropylisoxazol-4-yl)methoxy)-[1,1'-biphenyl]-3-carboxylic Acid (BAR2226)

Purification by HPLC on a Nucleodur Sphinx RP C18 column (5 μm; 4.6 mm i.d.×250 mm) with MeOH/$H_2O$ (80:20) as eluent (flow rate 1 mL/min), furnished pure BAR2226 ($t_R$=13.3 min).

$^1$H NMR (CDCl$_3$, 400 MHz): δ 8.26 (1H, br s) 8.04 (1H, d, J 7.77 Hz), 7.77 (1H, d, J=7.77 Hz), 7.64 (2H, d, J=8.08 Hz), 7.53 (1H, t, J=7.77 Hz), 7.51 (2H, d, J=8.78 Hz), 7.18 (1H, t, J=8.08 Hz), 6.90 (2H, d, J=8.78 Hz), 4.79 (2H, s), 3.37 (1H, septet, J=7.03 Hz), 1.45 (6H, d, J=7.03 Hz).

$^{13}$C NMR (CDCl$_3$, 100 MHz): δ 176.5, 171.4, 161.9, 158.1, 140.7, 132.8, 131.9, 131.8, 130.8, 129.7, 128.7, 128.3, 128.2, 128.2 (2C), 124.9, 124.1, 123.9, 115.0 (2C), 108.9, 59.4, 27.1, 20.8 (2C).

Example 5F. Preparation of 4'-((3-(2,6-dichlorophenyl)-5-methylisoxazol-4-yl)methoxy)-[1,1'-biphenyl]-3-carboxylic Acid (BAR2227)

Purification by silica gel, after step c, gave BAR2227 (98%). An analytic sample was obtained by HPLC on a Luna C18 (5 μm; 4.6 mm i.d.×250 mm), with a linear gradient of buffer B from 40% to 95% in 13 min (buffer A=95 $H_2O$: 5 $CH_3CN$: 0.1 TFA; buffer B=95 $CH_3CN$: 5 $H_2O$: 0.1 TFA) as eluent (flow rate 1.5 mL/min) ($t_R$=13.3 min).

BAR2227 $C_{24}H_{17}Cl_2NO_4$ $^1$H NMR (CDCl$_3$, 400 MHz): δ 8.27 (1H, s), 8.04 (1H, d, J=7.7 Hz), 7.77 (1H, d, J=7.7 Hz), 7.51 (2H, d, J=8.2 Hz), 7.53 (1H, t, J=7.7 Hz), 7.43 (2H, d, J=8.0 Hz), 7.34 (1H, t, J=8.0 Hz), 6.89 (2H, d, J=8.2 Hz), 4.80 (2H, s), 2.59 (3H, s);

$^{13}$C NMR (CDCl$_3$, 100 MHz): δ 168.6, 165.4, 159.0, 158.1, 141.0, 135.8 (2C), 133.1, 131.8 (2C), 131.3, 129.0, 128.5, 128.4, 128.2 (2C), 128.1 (2C), 127.8, 115.1 (2C), 111.2, 59.7, 11.6.

Example 5G. Preparation of 4'-((3-(2,6-dichlorophenyl)-5-propylisoxazol-4-yl)methoxy)-[1,1'-biphenyl]-3-carboxylic Acid (BAR2228)

Purification by silica gel, after step c, gave BAR2228 (quantitative yield). An analytic sample was obtained by HPLC on a Luna C18 (5 μm; 4.6 mm i.d.×250 mm), with a linear gradient of buffer B from 40% to 95% in 13 min (buffer A=95 $H_2O$: 5 $CH_3CN$: 0.1 TFA; buffer B=95 $CH_3CN$: 5 $H_2O$: 0.1 TFA) as eluent (flow rate 1.5 mL/min) ($t_R$=14.7 min).

BAR2228 $C_{26}H_{21}Cl_2NO_4$ $^1$H NMR (CDCl$_3$, 400 MHz): δ 8.26 (1H, s), 8.04 (1H, d, J=7.8 Hz), 7.76 (1H, d, J=7.8 Hz), 7.50 (2H, d, J=8.5 Hz), 7.52 (1H, t, J=7.8 Hz), 7.42 (2H, d, J=8.0 Hz), 7.34 (1H, t, J=8.0 Hz), 6.88 (2H, d, J=8.5 Hz), 4.78 (2H, s), 2.91 (2H, t, J=7.3 Hz), 1.86 (2H, sextet, J=7.3 Hz), 1.04 (3H, t, J=7.3 Hz);

$^{13}$C NMR (CDCl$_3$, 100 MHz): δ 172.2, 165.2, 159.0, 158.1, 141.0, 135.8 (2C), 133.0, 131.9, 131.3 (2C), 129.0, 128.5, 128.4, 128.2 (2C), 128.1 (2C), 127.9, 115.1 (2C), 111.0, 59.5, 27.9, 21.1, 13.6.

Example 6. Biological Activity

The biological activity of the selected compounds (Table 1) was tested in vitro using a cell model transfected with reporter genes, on the receptor FXR in comparison with the control agonist, chenodeoxycholic acid (CDCA), a primary bile acid that functions as an endogenous ligand of the receptor.

HepG2 cells were cultured at 37° C. in E-MEM medium (Earl's salt Minimum Essential Medium) with the addition of 10% fetal bovine serum (FBS), 1% L-glutamine, and 1% penicillin/streptomycin. The transfection experiments were performed using the reagent Fugene HD (Promega) according to the manufacturer's instructions. The cells were plated in 24-well plates at 5×10$^4$ cells/well.

HepG2 cells were transfected with 100 ng of the vector pSG5-FXR, 100 ng of the vector pSG5-RXR, 100 ng of the vector pGL4.70 *Renilla*, a plasmid encoding the human *Renilla* gene, and 200 ng of the reporter vector p(hsp27)-TK-LUC containing the FXR responsive-element IR1 cloned from the promoter of heat shock protein 27 (hsp27).

At 24 h post transfection, cells were stimulated with compounds and CDCA as positive control. To evaluate the EC$_{50}$, dose-response curves were performed in HepG2 cells transfected as described and treated with increasing concentrations of compounds (0.1, 0.5, 1, 2.5, 5, 7.5, 10, 12.5, 25 and 50 μM) (Table 1). After treatments, cells were lysed in 100 μL of lysis buffer (25 mM Tris-phosphate, pH 7.8; 2 mM DTT; 10% glycerol; 1% Triton X-100); 10 μL of the cellular lysate of each sample were assayed for luciferase activity using Dual Luciferase Reporter Assay System (Promega Italia S.r.l., Milan, Italy) according to the manufacturer's instructions. Luminescence was measured using Glomax 20/20 luminometer (Promega Italia S.r.l., Milan, Italy). The luciferase activity (Luciferase Recording Unit, RLU) was normalized using the activity of the *Renilla* (*Renilla* Recording Unit, RRU).

Activation of FXR has been also measured in cell-free assay by Alpha Screen Technology in a Coactivator Recruitment Assay. Anti-GST-coated acceptor beads were used to capture the GST-fusion FXR-LBD, whereas the biotinylated-SRC-1 peptide was captured by the streptavidin donor beads. Upon illumination at 680 nm, chemical energy is transferred from donor to acceptor beads across the complex streptavidin-donor/SRC-1-biotin/GSTFXR-LBD/anti-GST-acceptor and a signal is produced. The assay has been performed in white, low-volume, 384-well Optiplates (PerkinElmer) using a final volume of 25 μL containing final concentrations of 10 nM of purified GST-tagged FXR-LBD protein, 30 nM biotinylated SRC-1 peptide, 20 mg/mL anti-GST acceptor beads, and 10 mg/mL of streptavidin donor bead (PerkinElmer). The assay buffer contained 50 mM Tris (pH 7.4), 50 mM KCl and 1 mM DTT. The stimulation times with 1 μL of tested compound (each at a final concentration of 5 μM) were fixed to 30 min at room temperature. The concentration of DMSO in each well was maintained at a final concentration of 2%. After the addition of the detection mix (acceptor and donor beads), the plates were incubated in the dark for 3 h at room temperature and then were read in an Envision microplate analyzer (PerkinElmer).

Table 1 reports the efficacy of the selected compounds included in Formula (I) in SRC-1 coactivator recruitment as percent of the maximum efficacy of the compound relative to CDCA set as 100%. Results are expressed as mean of three independent measurements±standard error. Each ligand was tested at 5 μM concentration.

Table 1 reports the potency of the selected compounds included in Formula (I) as EC$_{50}$ values (μM) calculated in transactivation assay from at least three experiments. Results are expressed as mean±standard error.

To investigate the specificity of compounds versus PPARγ, HepG2 cells were transiently transfected with 200 ng reporter vector p(UAS)5XTKLuc, 100 ng pGL4.70 and with a vector containing the ligand binding domain of nuclear receptor PPARγ cloned upstream of the GAL4-DNA binding domain (pSG5-PPARγLBD-GAL4DBD).

To investigate the specificity of compounds versus GPBAR1, HEK-293T cells were transiently transfected with Fugene HD reagent (Promega) using the following vectors: pCMVSPORT6-human GPBAR1, pGL4.29 (Promega), a reporter vector containing a cAMP response element (CRE) cloned upstream to the luciferase reporter gene luc2P and pGL4.70.

To investigate the specificity of compounds versus LXRα and LXRβ mediated transactivation, HepG2 cells were transfected with 200 ng of the reporter vector p(UAS)5XTKLuc, 100 ng of a vector containing the ligand binding domain of LXRα or LXRβ cloned upstream of the GAL4-DNA binding domain (i.e. pSG5-LXRαLBD-GAL4DBD or pSG5-LXRβLBD-GAL4DBD) and 100 of pGL4.70 (Promega), a vector encoding the human *Renilla* gene.

At 24 h post transfection, cells were stimulated with specific receptor agonists GW3965 (10 μM), Rosiglitazon (500 nM) and TLCA (10 μM) respectively, or with compounds (10 μM).

At 18 h post stimulations, cellular lysate was assayed for luciferase and *Renilla* activities using the Dual-Luciferase Reporter assay system (E1980, Promega). Luminescence was measured using Glomax 20/20 luminometer (Promega). Luciferase activities were normalized with *Renilla* activities.

None of the compounds belonging to Formula (I) showed agonistic/antagonistic activity on LXRs, PPARγ and GPBAR1.

RNA isolation and RT-PCR. HepG2 cells were plated at the density of 1×10$^6$ cells/flask in T25 flask. After an overnight incubation, cells were starved and then stimulated for 18 h with 10 μM GW3965 or compounds (0.1, 1 and 5 μM).

Total RNA was isolated from HepG2 cells or liver tissue using the TRIzol reagent according to the manufacturer's specifications (Invitrogen). One microgram of purified RNA was treated with DNase-I and reverse transcribed with QuantiTect Reverse Transcription Kit (Qiagen). For Real Time PCR, 10 ng template was dissolved in 25 μL containing 200 nmol/L of each primer and 12.5 μL of 2×SYBR FAST Universal ready mix (Invitrogen). All reactions were performed in triplicate, and the thermal cycling conditions were as follows: 2 min at 95° C., followed by 40 cycles of 95° C. for 20 s and 60° C. for 30 s in StepOnePlus (Applied Biosystems). The relative mRNA expression was calculated in accord to the Ct method. Forward and reverse primer sequences were the following: human GAPDH: gaaggtgaaggtcggagt (SEQ ID: 1) and catgggtggaatcatattggaa (SEQ ID: 2); human SHP: gctgtctggagtccttctgg (SEQ ID: 3) and ccaatgatagggcgaaagaag (SEQ ID: 4); mouse GAPDH, ctgagtatgtcgtggagtctac (SEQ ID: 5) and gttggtggtgcaggatgcattg (SEQ ID: 6); mouse SHP acgatcctcttcaacccaga (SEQ ID: 7) and agggctccaagacttcacac (SEQ ID: 8); mouse FXR: agcttccagggtttcagaca (SEQ ID: 9) and cttccaacaggtctgcatga (SEQ ID: 10); mouse BSEP: gatgcttcccaagttcaagg (SEQ ID: 11) and taaagaggaaggcgatgagc (SEQ ID: 12).

Animals and Protocols.

C57BL/6N male mice were from The Jackson's Laboratory. Mice were housed under controlled temperatures (22° C.) and photoperiods (12:12-hour light/dark cycle), allowed unrestricted access to standard mouse chow and tap water and allowed to acclimate to these conditions for at least 5 days before inclusion in an experiment. The experimental protocol was approved by the Animal Care and Use Committee of the University of Perugia and by the Italian Minister of Health and Istituto Superiore di Sanità (Italy) and were in agreement with the European guidelines for use of experimental animals (permission n. 214/2017-PR). The general health of the animals was monitored daily by the Veterinarian in the animal facility. To evaluate the in vivo intestinal absorption and the successful transport to the liver, mice were administered with 10 mg/kg of BAR2109 dissolved in methylcellulose, daily by gavage (OS) or I.P. for 3 days. At the end of the treatment the animals were sacrificed and blood and liver collected for further analysis.

Microsomal Stability.

Male mouse (CD-1) liver microsomes (Sigma-Aldrich) were used. All incubations were performed in duplicate in a shaking water bath at 37° C. The incubation mixtures contained 1 μM compound with 1% DMSO used as a vehicle, mouse liver microsomes (0.3 mg of microsomal protein per mL), 5 mM $MgCl_2$, 1 mM NADP, 5 mM glucose 6-phosphate, 0.4 $U·mL^{-1}$ glucose 6-phosphate dehydrogenase, and 50 mM potassium phosphate buffer (pH 7.4) in a final volume of 0.5 mL. Aliquots were removed at 0, 5, 10, 20, 30, and 40 min after microsome addition and the reaction was stopped by adding 200 μL of ice-cold acetonitrile. After 2 h, the samples were centrifuged for 10 min at 10000 rpm, and the supernatants were transferred in matrix tubes for LC-MS/MS analysis. Propranolol, known as a high hepatic clearance drug in rodents, was used as a quality-control compound for the microsomal incubations. The slope of the linear regression of the curve obtained reporting the natural logarithm of compound area versus incubation time (–k) was used in the conversion to in vitro $t_{1/2}$ values by $t_{1/2}=-\ln(2)/k$. In vitro intrinsic clearance ($CL_{int}$ expressed as μL/min/mg) was calculated according to the following formula: Clint=volume of reaction (μL)/$t_{1/2}$ (min)/protein of liver microsomes (mg). The percentage of unmodified compound has been calculated assuming the area of the compound peak at time 0 min as 100%.

TABLE 1

| Compound | Efficacy (%) vs CDCA | $EC_{50}$ |
|---|---|---|
| CDCA | — | |
| EAR2101 | 114 ± 7 | 1.59 ± 0.35 |
| EAR2102 | 136 ± 7 | 3.59 ± 1.08 |
| EAR2103 | 151 ± 6 | 0.81 ± 0.20 |
| EAR2104 | 164 ± 18 | 2.93 ± 1.09 |
| EAR2105 | 43 ± 18 | 6.67 ± 1.7 |
| EAR2106 | 92 ± 1 | 0.73 ± 0.07 |
| EAR2107 | 83 ± 2 | 0.94 ± 0.02 |
| EAR2108 | 103 ± 4 | 0.74 ± 0.02 |
| EAR2109 | 149 ± 12 | 0.30 ± 0.006 |
| EAR2110 | 120 ± 6 | 2.06 ± 0.26 |
| EAR2111 | 67 ± 18 | 19.74 ± 0.31 |
| EAR2112 | 76 ± 20 | 4.37 ± 0.72 |
| EAR2113 | 93 ± 17 | 10.17 ± 0.84 |
| EAR2116 | 167 ± 7 | 1.09 ± 0.1 |
| EAR2118 | 125 ± 3 | 2.8 ± 0.36 |
| EAR2119 | 175 ± 3 | 1.4 ± 0.32 |
| EAR2120 | 121 ± 2 | 0.83 ± 0.06 |
| EAR2121 | 117 ± 5 | 5.4 ± 0.51 |
| BAR2122 | 97 ± 3 | 1.15 ± 0.37 |
| BAR2123 | 191 ± 4 | 0.46 ± 0.033 |
| BAR2124 | 124 ± 14 | 0.67 ± 0.038 |
| BAR2139 | 146 ± 4 | 1.5 ± 0.2 |
| BAR2222 | 95 ± 10 | 1.8 ± 0.4 |
| BAR2223 | 114 ± 0.1 | 2.4 ± 0.4 |
| BAR2224 | 60 ± 8 | 2.1 ± 0.5 |
| BAR2225 | 134 ± 4 | 1.0 ± 0.5 |
| BAR2226 | 160 ± 6 | 1.4 ± 0.5 |
| BAR2227 | 82 ± 19 | 3.6 ± 1.2 |
| BAR2228 | 221 ± 30 | 3.2 ± 2.3 |

Preferred examples included in the general formula are BAR2119 ($Cl_{int}$ 53 μL/min/mg, $t_{1/2}$ (min) 44), BAR2109 ($Cl_{int}$ 32 μL/min/mg, $t_{1/2}$ (min) 72) and BAR2123 ($Cl_{int}$ 35 μL/min/mg, (min) 66) showing increased in vitro metabolic stability respect to the reference compound GW4064 ($Cl_{int}$ 56 μL/min/mg, t (min) 41).

Preferred examples included in the general formula are BAR2109 and BAR2123 inducing SHP mRNA expression at 5 μM concentration of 6.8 times and 6.2 times, respectively (reference compound GW4064 tested at 10 μM concentration; SHP mRNA expression induction=4.2 times).

Preferred example included in the general formula is BAR2109 inducing liver SHP mRNA and BSEP mRNA expression when administered per os.

The invention claimed is:

1. Compound of formula (I):

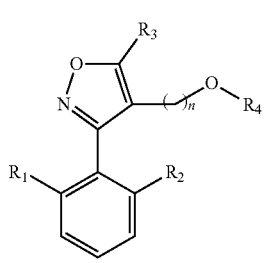

wherein $R_1$ and $R_2$ are independently selected from the group consisting of H, halogen, and $CF_3$ provided that $R_1$ and $R_2$ are not H at the same time;

$R_3$ is selected from the group consisting of $C_1$-$C_3$alkyl and halo-$C_1$-$C_3$alkyl;

n is an integer selected from 1, 2 and 3;

$R_4$ is selected from the group consisting of phenyl unsubstituted or substituted with one $R_5$ and biphenyl unsubstituted or substituted with one $R_5$;

$R_5$ is selected from the group consisting of $COOR_6$, CN, hydroxy-$C_1$-$C_3$alkyl, $SO_2CH_3$, $CF_3$, $C_1$-$C_3$alkyl-O-phenyl unsubstituted or substituted with one $R_7$ and $C_1$-$C_3$alkyl-O-biphenyl unsubstituted or substituted with one $R_7$;

$R_6$ is selected from the group consisting of H and $C_1$-$C_3$alkyl and $R_7$ is selected from the group consisting of $COOR_6$, CN, hydroxy-$C_1$-$C_3$alkyl, $SO_2CH_3$ and $CF_3$;

provided that the compound is not 4-((3-(2,6-dichlorophenyl)-5-isopropylisoxazol-4-yl)methoxy)benzoic acid.

2. Compound according to claim 1, wherein $R_4$ is selected from the group consisting of

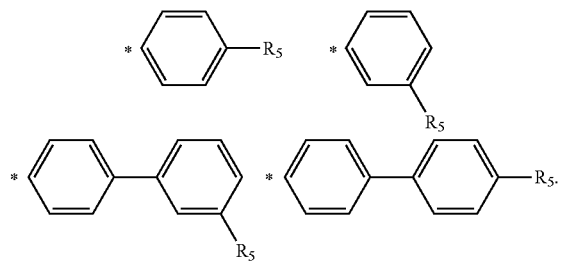

3. Compound according to claim 1, wherein $R_5$ is selected from the group consisting of COOH, COOCH$_3$, CN, —CH$_2$OH, SO$_2$CH$_3$,

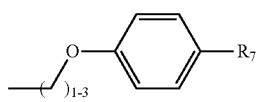

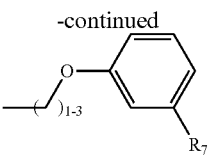

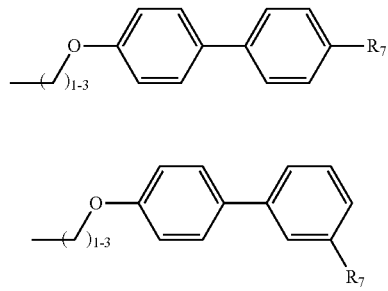

4. Compound according to claim 1, wherein the compound of formula (I) is selected from the group consisting of:

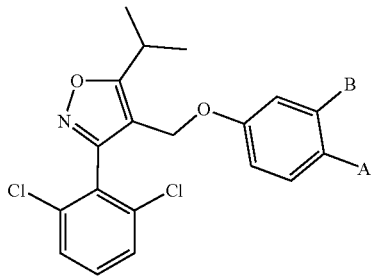

| | | |
|---|---|---|
| A = H | B = H | BAR2101 |
| A = COOMe | B = H | BAR2102 |
| A = CN | B = H | BAR2103 |
| A = CH$_2$OH | B = H | BAR2104 |
| A = CF$_3$ | B = H | BAR2115 |
| A = SO$_2$Me | B = H | BAR2116 |
| A = H | B = COOMe | BAR2110 |
| A = H | B = COOH | BAR2111 |
| A = H | B = CH$_2$OH | BAR2112 |
| A = H | B = CN | BAR2113 |
| A = H | B = CF$_3$ | BAR2114 |
| A = H | B = SO$_2$Me | BAR2117 |

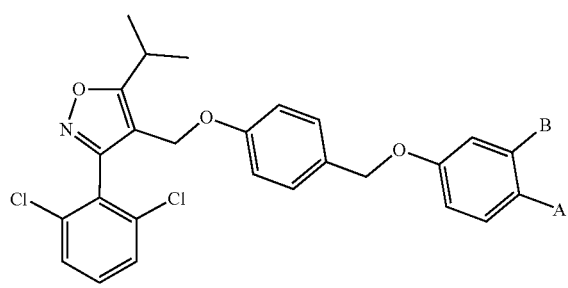

| | | |
|---|---|---|
| A = COOMe | B = H | BAR2106 |
| A = CN | B = H | BAR2107 |
| A = CH$_2$OH | B = H | BAR2108 |
| A = COOH | B = H | BAR2109 |
| A = SO$_2$Me | B = H | BAR2125 |
| A = CF$_3$ | B = H | BAR2126 |
| A = H | B = CN | BAR2121 |
| A = H | B = COOMe | BAR2122 |

-continued

| | | |
|---|---|---|
| A = H | B = COOH | BAR2123 |
| A = H | B = CH$_2$OH | BAR2124 |
| A = H | B = SO$_2$Me | BAR2127 |
| A = H | B = CF$_3$ | BAR2128 |

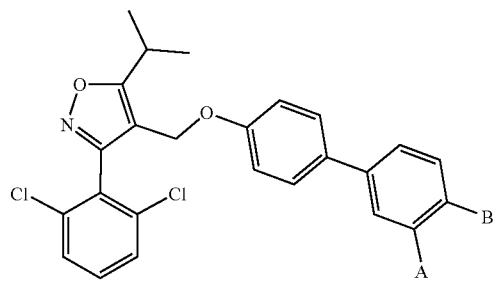

| | | |
|---|---|---|
| A = COOMe | B = H | BAR2118 |
| A = COOH | B = H | BAR2119 |
| A = CH$_2$OH | B = H | BAR2120 |
| A = CN | B = H | BAR2129 |
| A = SO$_2$Me | B = H | BAR2130 |
| A = CF$_3$ | B = H | BAR2131 |
| A = H | B = COOMe | BAR2132 |
| A = H | B = CN | BAR2133 |
| A = H | B = CH$_2$OH | BAR2134 |
| A = H | B = COOH | BAR2135 |
| A = H | B = SO$_2$Me | BAR2136 |
| A = H | B = CF$_3$ | BAR2137 |

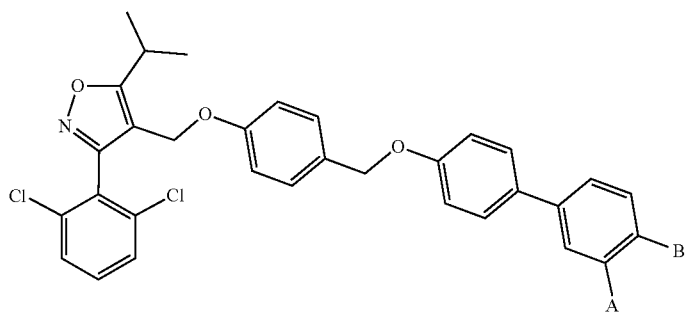

| | | |
|---|---|---|
| A = COOMe | B = H | BAR2138 |
| A = COOH | B = H | BAR2139 |
| A = CH$_2$OH | B = H | BAR2140 |
| A = CN | B = H | BAR2141 |
| A = SO$_2$Me | B = H | BAR2142 |
| A = CF3 | B = H | BAR2143 |
| A = H | B = COOMe | BAR2144 |
| A = H | B = CN | BAR2145 |
| A = H | B = CH$_2$OH | BAR2146 |
| A = H | B = COOH | BAR2147 |
| A = H | B = SO$_2$Me | BAR2148 |
| A = H | B = CF$_3$ | BAR2149 |

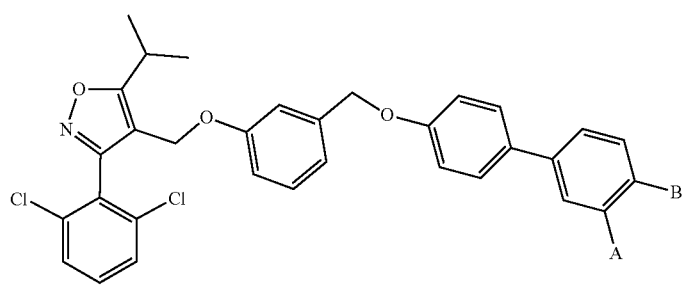

| | | |
|---|---|---|
| A = COOMe | B = H | BAR2150 |
| A = COOH | B = H | BAR2151 |
| A = CH$_2$OH | B = H | BAR2152 |
| A = CN | B = H | BAR2153 |
| A = SO$_2$Me | B = H | BAR2154 |

-continued

| | | |
|---|---|---|
| A = CF₃ | B = H | BAR2155 |
| A = H | B = COOMe | BAR2156 |
| A = H | B = CN | BAR2157 |
| A = H | B = CH₂OH | BAR2158 |
| A = H | B = COOH | BAR2159 |
| A = H | B = SO₂Me | BAR2160 |
| A = H | B = CF₃ | BAR2161 |

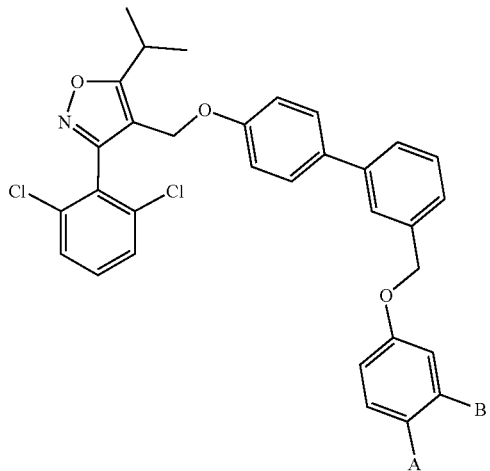

| | | |
|---|---|---|
| A = COOMe | B = H | BAR2162 |
| A = COOH | B = H | BAR2163 |
| A = CH₂OH | B = H | BAR2164 |
| A = CN | B = H | BAR2165 |
| A = SO₂Me | B = H | BAR2166 |
| A = CF₃ | B = H | BAR2167 |
| A = H | B = COOMe | BAR2168 |
| A = H | B = CN | BAR2169 |
| A = H | B = CH₂OH | BAR2170 |
| A = H | B = COOH | BAR2171 |
| A = H | B = SO₂Me | BAR2172 |
| A = H | B = CF₃ | BAR2173 |

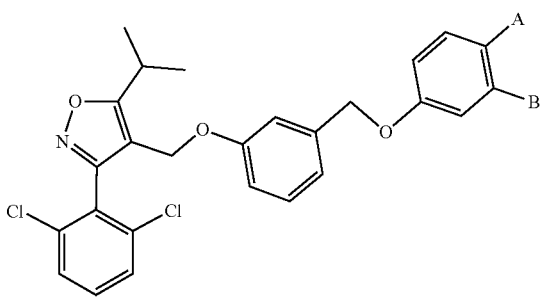

| | | |
|---|---|---|
| A = COOMe | B = H | BAR2174 |
| A = COOH | B = H | BAR2175 |
| A = CH₂OH | B = H | BAR2176 |
| A = CN | B = H | BAR2177 |
| A = SO₂Me | B = H | BAR2178 |
| A = CF₃ | B = H | BAR2179 |
| A = H | B = COOMe | BAR2180 |
| A = H | B = CN | BAR2181 |
| A = H | B = CH₂OH | BAR2182 |
| A = H | B = COOH | BAR2183 |
| A = H | B = SO₂Me | BAR2184 |
| A = H | B = CF₃ | BAR2185 |

-continued
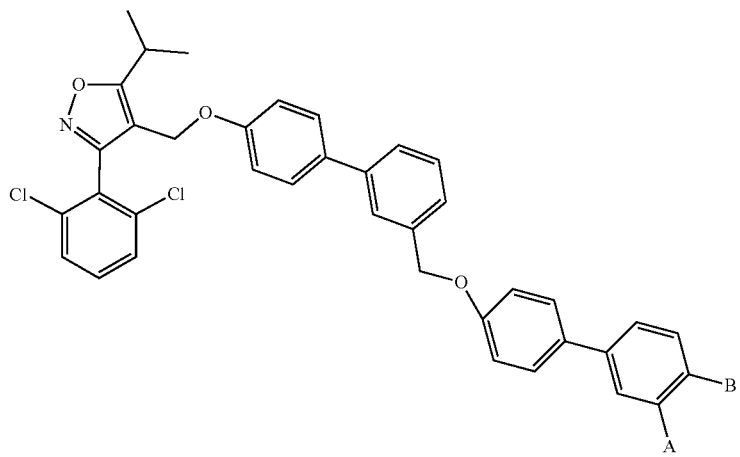
| | | |
|---|---|---|
| A = COOMe | B = H | BAR2186 |
| A = COOH | B = H | BAR2187 |
| A = CH₂OH | B = H | BAR2188 |
| A = CN | B = H | BAR2189 |
| A = SO₂Me | B = H | BAR2190 |
| A = CF₃ | B = H | BAR2191 |
| A = H | B = COOMe | BAR2192 |
| A = H | B = CN | BAR2193 |
| A = H | B = CH₂OH | BAR2194 |
| A = H | B = COOH | BAR2195 |
| A = H | B = SO₂Me | BAR2196 |
| A = H | B = CF₃ | BAR2197 |
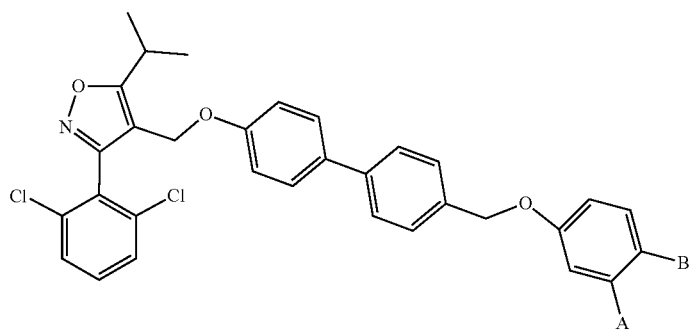
| | | |
|---|---|---|
| A = COOMe | B = H | BAR2198 |
| A = COOH | B = H | BAR2199 |
| A = CH₂OH | B = H | BAR2200 |
| A = CN | B = H | BAR2201 |
| A = SO₂Me | B = H | BAR2202 |
| A = CF₃ | B = H | BAR2203 |
| A = H | B = COOMe | BAR2204 |
| A = H | B = CN | BAR2205 |
| A = H | B = CH₂OH | BAR2206 |
| A = H | B = COOH | BAR2207 |
| A = H | B = SO₂Me | BAR2208 |
| A = H | B = CF₃ | BAR2209 |

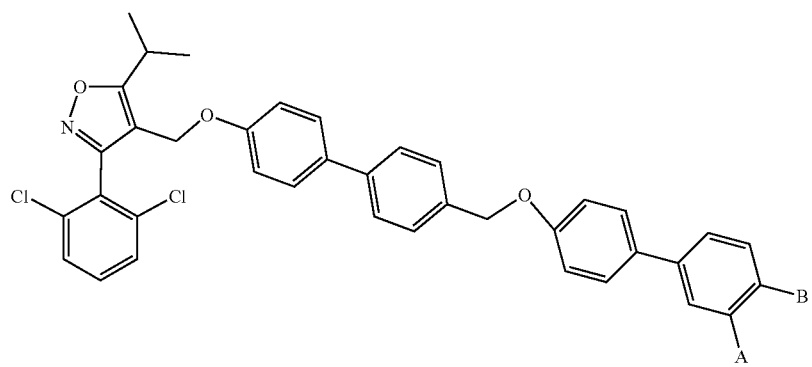
| | | |
|---|---|---|
| A = COOMe | B = H | BAR2210 |
| A = COOH | B = H | BAR2211 |
| A = CH₂OH | B = H | BAR2212 |
| A = CN | B = H | BAR2213 |
| A = SO₂Me | B = H | BAR2214 |
| A = CF₃ | B = H | BAR2215 |
| A = H | B = COOMe | BAR2216 |
| A = H | B = CN | BAR2217 |
| A = H | B = CH₂OH | BAR2218 |
| A = H | B = COOH | BAR2219 |
| A = H | B = SO₂Me | BAR2220 |
| A = H | B = CF₃ | BAR2221 |
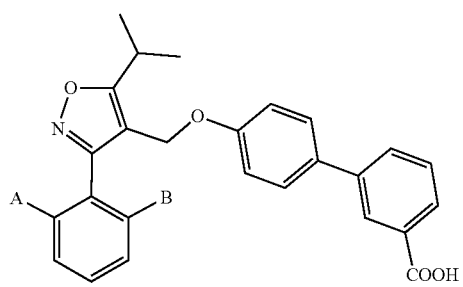
| | | |
|---|---|---|
| A = H | B = Cl | BAR2222 |
| A = H | B = Br | BAR2223 |
| A = H | B = CF₃ | BAR2224 |
| A = Br | B = Cl | BAR2225 |
| A = Br | B = Br | BAR2226 |
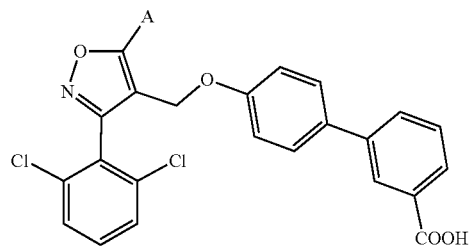
| | |
|---|---|
| A = -CH₃ | BAR2227 |
| A = -(CH₂)₂CH₃ | BAR2228 |

5. Pharmaceutical composition comprising a compound of formula (I):

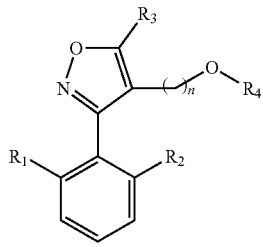

wherein $R_1$ and $R_2$ are independently selected from the group consisting of H, halogen, and $CF_3$ provided that $R_1$ and $R_2$ are not H at the same time;

$R_3$ is selected from the group consisting of $C_1$-$C_3$ alkyl and halo-$C_1$-$C_3$ alkyl;

n is an integer selected from 1, 2 and 3;

$R_4$ is selected from the group consisting of phenyl unsubstituted or substituted with one $R_5$ and biphenyl unsubstituted or substituted with one $R_5$;

$R_5$ is selected from the group consisting of $COOR_6$, CN, hydroxy-$C_1$-$C_3$alkyl, $SO_2CH_3$, $CF_3$, $C_1$-$C_3$ alkyl-O-phenyl unsubstituted or substituted with one $R_7$ and $C_1$-$C_3$alkyl-O-biphenyl unsubstituted or substituted with one $R_7$;

$R_6$ is selected from the group consisting of H and $C_1$-$C_3$alkyl and $R_7$ is selected from the group consisting of $COOR_6$, CN, hydroxy-$C_1$-$C_3$alkyl, $SO_2CH_3$ and $CF_3$;

or pharmaceutically acceptable salts and solvates thereof and at least one pharmaceutically acceptable excipient.

6. A method of treating an FXR-mediated disorder comprising administering to a subject in need thereof a pharmaceutically effective amount of an FXR agonist, wherein the FXR agonist is a compound of formula (I):

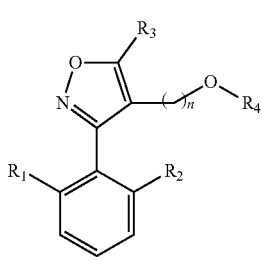

wherein $R_1$ and $R_2$ are independently selected from the group consisting of H, halogen, and $CF_3$ provided that $R_1$ and $R_2$ are not H at the same time;

$R_3$ is selected from the group consisting of $C_1$-$C_3$alkyl and halo-$C_1$-$C_3$alkyl;

n is an integer selected from 1, 2 and 3;

$R_4$ is selected from the group consisting of phenyl unsubstituted or substituted with one $R_5$ and biphenyl unsubstituted or substituted with one $R_5$;

$R_5$ is selected from the group consisting of $COOR_6$, CN, hydroxy-$C_1$-$C_3$alkyl, $SO_2CH_3$, $CF_3$, $C_1$-$C_3$alkyl-O-phenyl unsubstituted or substituted with one $R_7$ and $C_1$-$C_3$alkyl-O-biphenyl unsubstituted or substituted with one $R_7$;

$R_6$ is selected from the group consisting of H and $C_1$-$C_3$alkyl and $R_7$ is selected from the group consisting of $COOR_6$, CN, hydroxy-$C_1$-$C_3$alkyl, $SO_2CH_3$ and $CF_3$;

or pharmaceutically acceptable salts and solvates thereof, wherein the disorder is selected from the group consisting of: systemic lupus erythematosus, rheumatoid arthritis, Sjogren's syndrome, scleroderma, spondyloarthritis, vasculitis, sarcoidosis, Mediterranean fever, polymyositis and dermatomyositis, Behcet's syndrome, acquired immune deficiency, hepatitis virus B and hepatitis virus C infections, Alzheimer's disease and other dementias, Parkinson's disease, amyotrophic lateral sclerosis and other motor neuron disorders, multiple sclerosis and other demyelinating diseases, myasthenia and muscular dystrophies, primary biliary cirrhosis, cerebrotendinous xanthomatosis, primary sclerosing cholangitis, drug-induced cholestasis, intrahepatic cholestasis of pregnancy, cholestasis associated with parenteral nutrition, cholestasis associated with bacterial proliferation or sepsis, autoimmune hepatitis, chronic viral hepatitis, alcoholic liver disease, non-alcoholic fatty liver disease, non-alcoholic steatohepatitis, liver transplantation, congenital hepatic fibrosis, hepatic granulomatous disease, intra- or extra-hepatic malignant tumor, Wilson's disease, hemochromatosis, alpha 1-antitrypsin deficiency, inflammatory bowel disease, Crohn's disease, ulcerative rectocolitis, indeterminate colitis, irritable bowel syndrome, bacterial proliferation in the gastrointestinal system, acute and chronic pancreatitis, bowel movement malabsorption, post-radiation colitis, microscopic colitis, diabetic nephropathy, hypertensive nephropathy, chronic glomerulonephritis, chronic graft glomerulonephritis, chronic tubulointerstitial diseases, kidney vascular disorders, atherosclerosis, arteriosclerosis, dyslipidaemia, hypercholesterolemia, hypertriglyceridemia, arterial hypertension, cardiac inflammatory disorders, myocarditis, endocarditis, cardiac ischemia, stable angina, unstable angina, myocardial infarction, cerebrovascular disorders, ischemic stroke, pulmonary hypertension, peripheral artery disease, peripheral artery occlusive disease, obliterative peripheral arteriopathy, asthma, cystic fibrosis, respiratory obstructive diseases, interstitial lung diseases, primary or secondary pulmonary fibrosis, insulin resistance, metabolic syndrome, type I and type II diabetes, hypoglycaemia, disorders of the adrenal cortex, failure of the adrenal cortex, obesity, liver cancer, cancers of the bile ducts, oesophageal cancer, pancreatic cancer, gastric cancer, colon-rectal cancer, breast cancer, and ovarian cancer.

7. The method of claim 6, wherein the compound of formula (I) is selected from the group consisting of:

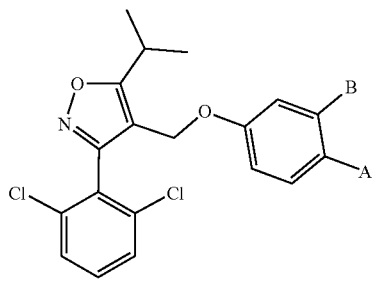

| | | |
|---|---|---|
| A = H | B = H | BAR2101 |
| A = COOMe | B = H | BAR2102 |
| A = CN | B = H | BAR2103 |
| A = CH₂OH | B = H | BAR2104 |
| A = COOH | B = H | BAR2105 |
| A = CF₃ | B = H | BAR2115 |
| A = SO₂Me | B = H | BAR2116 |
| A = H | B = COOMe | BAR2110 |
| A = H | B = COOH | BAR2111 |
| A = H | B = CH₂OH | BAR2112 |
| A = H | B = CN | BAR2113 |
| A = H | B = CF₃ | BAR2114 |
| A = H | B = SO₂Me | BAR2117 |

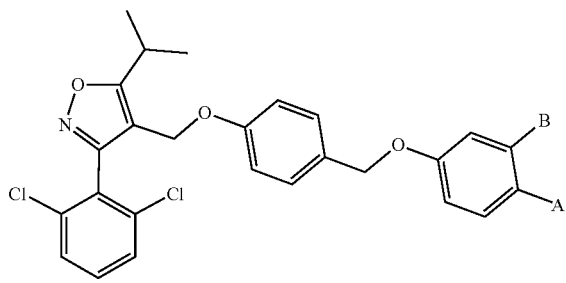

| | | |
|---|---|---|
| A = COOMe | B = H | BAR2106 |
| A = CN | B = H | BAR2107 |
| A = CH₂OH | B = H | BAR2108 |
| A = COOH | B = H | BAR2109 |
| A = SO₂Me | B = H | BAR2125 |
| A = CF₃ | B = H | BAR2126 |
| A = H | B = CN | BAR2121 |
| A = H | B = COOMe | BAR2122 |
| A = H | B = COOH | BAR2123 |
| A = H | B = CH₂OH | BAR2124 |
| A = H | B = SO₂Me | BAR2127 |
| A = H | B = CF₃ | BAR2128 |

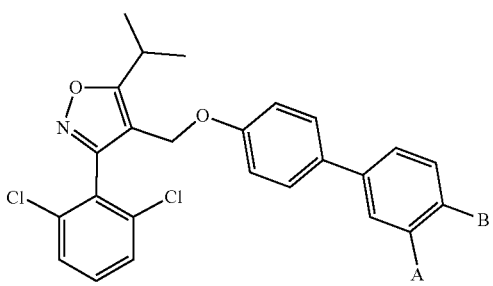

| | | |
|---|---|---|
| A = COOMe | B = H | BAR2118 |
| A = COOH | B = H | BAR2119 |
| A = CH₂OH | B = H | BAR2120 |
| A = CN | B = H | BAR2129 |
| A = SO₂Me | B = H | BAR2130 |
| A = CF₃ | B = H | BAR2131 |
| A = H | B = COOMe | BAR2132 |
| A = H | B = CN | BAR2133 |
| A = H | B = CH₂OH | BAR2134 |
| A = H | B = COOH | BAR2135 |
| A = H | B = SO₂Me | BAR2136 |
| A = H | B = CF₃ | BAR2137 |

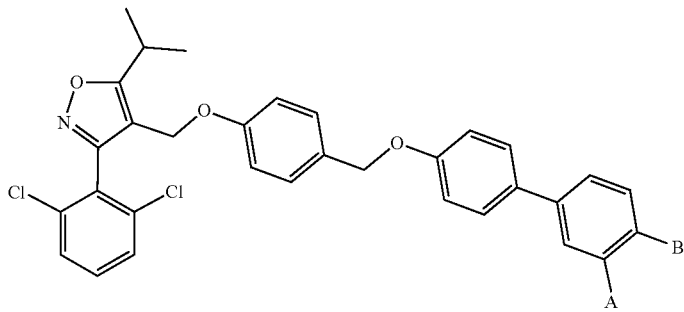
| | | |
|---|---|---|
| A = COOMe | B = H | BAR2138 |
| A = COOH | B = H | BAR2139 |
| A = CH₂OH | B = H | BAR2140 |
| A = CN | B = H | BAR2141 |
| A = SO₂Me | B = H | BAR2142 |
| A = CF₃ | B = H | BAR2143 |
| A = H | B = COOMe | BAR2144 |
| A = H | B = CN | BAR2145 |
| A = H | B = CH₂OH | BAR2146 |
| A = H | B = COOH | BAR2147 |
| A = H | B = SO₂Me | BAR2148 |
| A = H | B = CF₃ | BAR2149 |
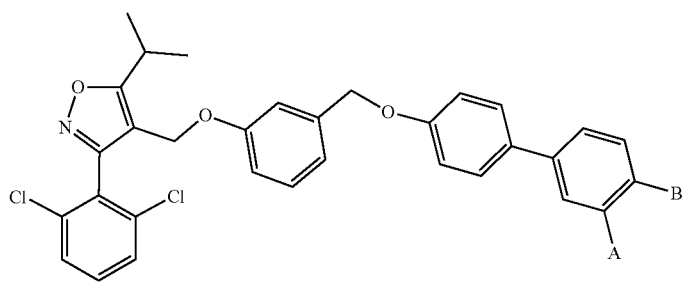
| | | |
|---|---|---|
| A = COOMe | B = H | BAR2150 |
| A = COOH | B = H | BAR2151 |
| A = CH₂OH | B = H | BAR2152 |
| A = CN | B = H | BAR2153 |
| A = SO₂Me | B = H | BAR2154 |
| A = CF₃ | B = H | BAR2155 |
| A = H | B = COOMe | BAR2156 |
| A = H | B = CN | BAR2157 |
| A = H | B = CH₂OH | BAR2158 |
| A = H | B = COOH | BAR2159 |
| A = H | B = SO₂Me | BAR2160 |
| A = H | B = CF₃ | BAR2161 |
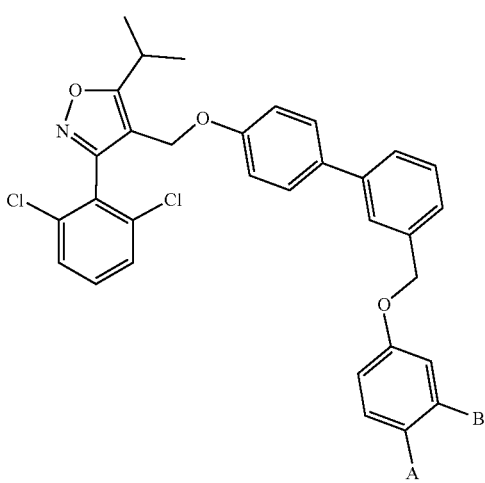

| | | |
|---|---|---|
| A = COOMe | B = H | BAR2162 |
| A = COOH | B = H | BAR2163 |
| A = CH$_2$OH | B = H | BAR2164 |
| A = CN | B = H | BAR2165 |
| A = SO$_2$Me | B = H | BAR2166 |
| A = CF$_3$ | B = H | BAR2167 |
| A = H | B = COOMe | BAR2168 |
| A = H | B = CN | BAR2169 |
| A = H | B = CH$_2$OH | BAR2170 |
| A = H | B = COOH | BAR2171 |
| A = H | B = SO$_2$Me | BAR2172 |
| A = H | B = CF$_3$ | BAR2173 |

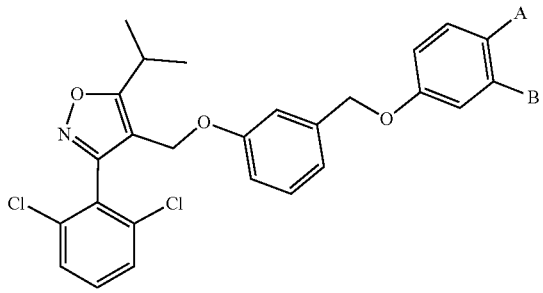

| | | |
|---|---|---|
| A = COOMe | B = H | BAR2174 |
| A = COOH | B = H | BAR2175 |
| A = CH$_2$OH | B = H | BAR2176 |
| A = CN | B = H | BAR2177 |
| A = SO$_2$Me | B = H | BAR2178 |
| A = CF$_3$ | B = H | BAR2179 |
| A = H | B = COOMe | BAR2180 |
| A = H | B = CN | BAR2181 |
| A = H | B = CH$_2$OH | BAR2182 |
| A = H | B = COOH | BAR2183 |
| A = H | B = SO$_2$Me | BAR2184 |
| A = H | B = CF$_3$ | BAR2185 |

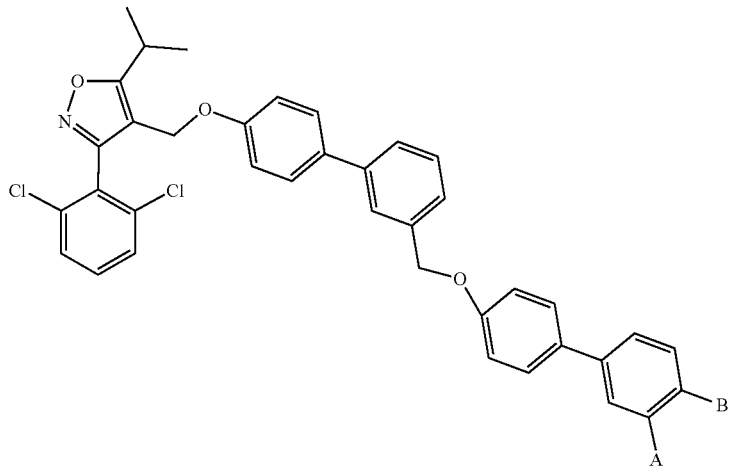

| | | |
|---|---|---|
| A = COOMe | B = H | BAR2186 |
| A = COOH | B = H | BAR2187 |
| A = CH$_2$OH | B = H | BAR2188 |
| A = CN | B = H | BAR2189 |
| A = SO$_2$Me | B = H | BAR2190 |
| A = CF$_3$ | B = H | BAR2191 |
| A = H | B = COOMe | BAR2192 |
| A = H | B = CN | BAR2193 |
| A = H | B = CH$_2$OH | BAR2194 |
| A = H | B = COOH | BAR2195 |
| A = H | B = SO$_2$Me | BAR2196 |
| A = H | B = CF$_3$ | BAR2197 |

-continued

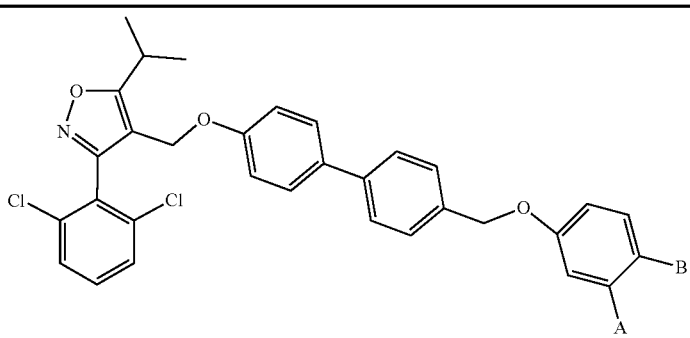

| | | |
|---|---|---|
| A = COOMe | B = H | BAR2198 |
| A = COOH | B = H | BAR2199 |
| A = CH₂OH | B = H | BAR2200 |
| A = CN | B = H | BAR2201 |
| A = SO₂Me | B = H | BAR2202 |
| A = CF₃ | B = H | BAR2203 |
| A = H | B = COOMe | BAR2204 |
| A = H | B = CN | BAR2205 |
| A = H | B = CH₂OH | BAR2206 |
| A = H | B = COOH | BAR2207 |
| A = H | B = SO₂Me | BAR2208 |
| A = H | B = CF₃ | BAR2209 |

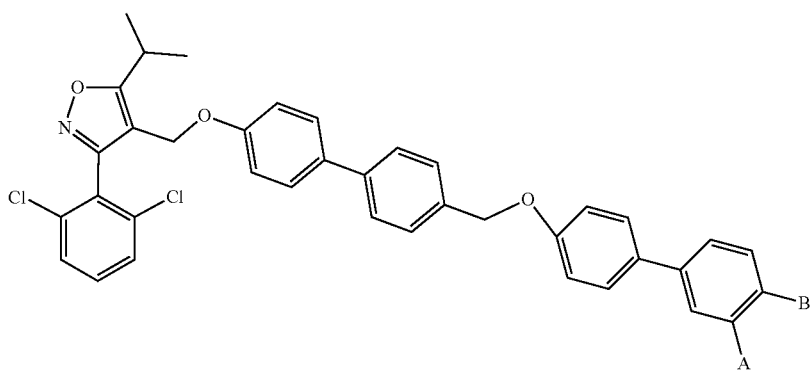

| | | |
|---|---|---|
| A = COOMe | B = H | BAR2210 |
| A = COOH | B = H | BAR2211 |
| A = CH₂OH | B = H | BAR2212 |
| A = CN | B = H | BAR2213 |
| A = SO₂Me | B = H | BAR2214 |
| A = CF₃ | B = H | BAR2215 |
| A = H | B = COOMe | BAR2216 |
| A = H | B = CN | BAR2217 |
| A = H | B = CH₂OH | BAR2218 |
| A = H | B = COOH | BAR2219 |
| A = H | B = SO₂Me | BAR2220 |
| A = H | B = CF₃ | BAR2221 |

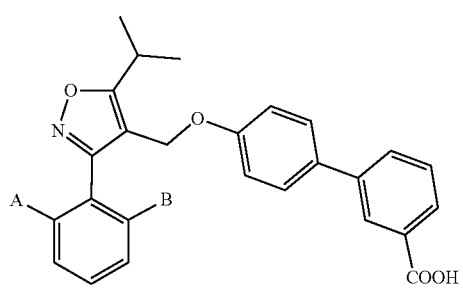

| | | |
|---|---|---|
| A = H | B = Cl | BAR2222 |
| A = H | B = Br | BAR2223 |
| A = H | B = CF₃ | BAR2224 |
| A = Br | B = Cl | BAR2225 |
| A = Br | B = Br | BAR2226 |

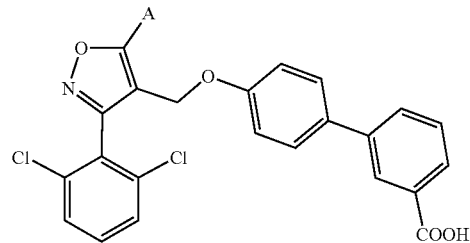
A = –CH₃     BAR2227
A = –(CH₂)₂CH₃     BAR2228
\* \* \* \* \*